(12) United States Patent
Arshonsky et al.

(10) Patent No.: US 10,357,311 B2
(45) Date of Patent: Jul. 23, 2019

(54) ELECTROSURGICAL INSTRUMENT WITH REMOVABLE JAW COMPONENTS

(71) Applicant: Ethicon Endo-Surgery, Inc., Cincinnati, OH (US)

(72) Inventors: Susan Arshonsky, Cincinnati, OH (US); Catherine A. Corbett, Cincinnati, OH (US); Megan A. Broderick, West Chester, OH (US); Geoffrey S. Strobl, Williamsburg, OH (US); Gregory A. Trees, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 637 days.

(21) Appl. No.: 14/576,372

(22) Filed: Dec. 19, 2014

(65) Prior Publication Data
US 2016/0175050 A1    Jun. 23, 2016

(51) Int. Cl.
| | | |
|---|---|---|
| *A61B 18/18* | (2006.01) | |
| *A61B 19/00* | (2006.01) | |
| *A61B 18/14* | (2006.01) | |
| *A61B 17/00* | (2006.01) | |
| *A61B 18/00* | (2006.01) | |

(52) U.S. Cl.
CPC .......... *A61B 18/18* (2013.01); *A61B 18/1445* (2013.01); *A61B 19/34* (2013.01); *A61B 2017/00477* (2013.01); *A61B 2018/0063* (2013.01); *A61B 2018/0097* (2013.01); *A61B 2018/1455* (2013.01); *A61B 2018/1495* (2013.01)

(58) Field of Classification Search
CPC ................... A61B 19/34; A61B 2018/0097
See application file for complete search history.

(56) References Cited

U.S. PATENT DOCUMENTS

| | | |
|---|---|---|
| 4,805,823 A | 2/1989 | Rothfuss |
| 5,415,334 A | 5/1995 | Williamson et al. |
| 5,465,895 A | 11/1995 | Knodel et al. |
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,814,055 A | 9/1998 | Knodel et al. |
| 6,245,070 B1 | 6/2001 | Marquis et al. |

(Continued)

OTHER PUBLICATIONS

U.S. Appl. No. 61/550,768, filed Oct. 24, 2011.

(Continued)

*Primary Examiner* — Linda C Dvorak
*Assistant Examiner* — Ryan T Clark
(74) *Attorney, Agent, or Firm* — Frost Brown Todd LLC

(57) ABSTRACT

A surgical instrument includes a body, an elongate shaft extending distally from the body, an end effector disposed at a distal end of the elongate shaft, and a firing beam. The end effector has a first jaw and a second jaw. The first jaw is pivotable toward and away from the second jaw to capture tissue. The end effector further comprises at least one electrode. The at least one electrode is operable to apply RF energy to tissue captured between the first jaw and the second jaw. At least a portion of the end effector is reconfigurable to transition the end effector into a cleaning state

20 Claims, 22 Drawing Sheets

(56) References Cited

U.S. PATENT DOCUMENTS

| | | | |
|---|---|---|---|
| 6,443,970 B1 * | 9/2002 | Schulze | A61B 18/1445 606/171 |
| 6,500,176 B1 | 12/2002 | Truckai et al. | |
| 6,783,524 B2 | 8/2004 | Anderson et al. | |
| 6,978,921 B2 | 12/2005 | Shelton et al. | |
| 7,000,818 B2 | 2/2006 | Shelton et al. | |
| 7,112,201 B2 | 9/2006 | Truckai et al. | |
| 7,125,409 B2 | 10/2006 | Truckai et al. | |
| 7,143,923 B2 | 12/2006 | Shelton et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,303,108 B2 | 12/2007 | Shelton | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,381,209 B2 | 6/2008 | Truckai et al. | |
| 7,404,508 B2 | 7/2008 | Smith et al. | |
| 7,343,715 B2 | 10/2008 | Ito et al. | |
| 7,434,715 B2 | 10/2008 | Shelton, IV et al. | |
| 7,721,930 B2 | 5/2010 | McKenna et al. | |
| 8,408,439 B2 | 4/2013 | Huang et al. | |
| 8,453,914 B2 | 6/2013 | Laurent et al. | |
| 8,461,744 B2 | 6/2013 | Wiener et al. | |
| 8,477,595 B2 | 7/2013 | Schousterman et al. | |
| 8,858,547 B2 | 10/2014 | Brogna | |
| 8,888,809 B2 | 11/2014 | Davison et al. | |
| 8,939,974 B2 | 1/2015 | Boudreaux et al. | |
| 8,951,248 B2 | 2/2015 | Messerly et al. | |
| 8,956,349 B2 | 2/2015 | Aldridge et al. | |
| 8,986,302 B2 | 3/2015 | Aldridge et al. | |
| 9,039,695 B2 | 5/2015 | Giordano et al. | |
| 9,039,732 B2 | 5/2015 | Sims et al. | |
| 9,050,093 B2 | 6/2015 | Aldridge et al. | |
| 9,060,776 B2 | 6/2015 | Yates et al. | |
| 9,089,327 B2 | 7/2015 | Worrell et al. | |
| 9,089,360 B2 | 7/2015 | Messerly et al. | |
| 9,161,803 B2 | 10/2015 | Yates et al. | |
| 9,220,559 B2 | 12/2015 | Worrell et al. | |
| 9,402,682 B2 | 8/2016 | Worrell et al. | |
| 2003/0018332 A1 * | 1/2003 | Schmaltz | A61B 18/1445 606/51 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0004656 A1 * | 1/2008 | Livneh | A61B 17/29 606/205 |
| 2008/0200940 A1 | 8/2008 | Eichmann et al. | |
| 2009/0030437 A1 * | 1/2009 | Houser | A61B 17/32009 606/169 |
| 2009/0088774 A1 * | 4/2009 | Swarup | A61B 34/37 606/130 |
| 2010/0249700 A1 * | 9/2010 | Spivey | A61B 17/00234 604/96.01 |
| 2011/0071543 A1 * | 3/2011 | Prisco | A61B 17/0218 606/130 |
| 2011/0306965 A1 * | 12/2011 | Norvell | A61B 18/1445 606/41 |
| 2012/0078243 A1 | 3/2012 | Worrell et al. | |
| 2012/0078244 A1 | 3/2012 | Worrell et al. | |
| 2012/0083826 A1 * | 4/2012 | Chao | A61B 17/00234 606/205 |
| 2012/0116433 A1 * | 5/2012 | Houser | A61B 17/00234 606/169 |
| 2013/0023868 A1 | 1/2013 | Worrell et al. | |
| 2013/0046295 A1 * | 2/2013 | Kerr | A61B 18/1445 606/41 |

OTHER PUBLICATIONS

International Search Report and Written Opinion dated May 30, 2016 for Application No. PCT/US2015/065505, 15 pgs.
U.S. Appl. No. 61/410,603, filed Nov. 5, 2010.

* cited by examiner

ELECTROSURGICAL INSTRUMENT WITH REMOVABLE JAW COMPONENTS

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. Pub. No. 2012/0083783, entitled "Surgical Instrument with Jaw Member," published Apr. 5, 2012, issued as U.S. Pat. No. 8,888,809 on Nov. 18, 2014, the disclosure of which is incorporated by reference herein; U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein; U.S. Pub. No. 2012/0078243, entitled "Control Features for Articulating Surgical Device," published Mar. 29, 2012, issued as U.S. Pat. No. 9,877,720 on Jan. 30, 2018, the disclosure of which is incorporated by reference herein; U.S. Pub. No. 2012/0078247, entitled "Articulation Joint Features for Articulating Surgical Device," published Mar. 29, 2012, issued as U.S. Pat. No. 9,402,682 on Aug. 2, 2016, the disclosure of which is incorporated by reference herein; U.S. Pub. No. 2013/0030428, entitled "Surgical Instrument with Multi-Phase Trigger Bias," published Jan. 31, 2013, issued as U.S. Pat. No. 9,089,327 on Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, issued as U.S. Pat. No. 9,545,253 Jan. 17, 2017, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
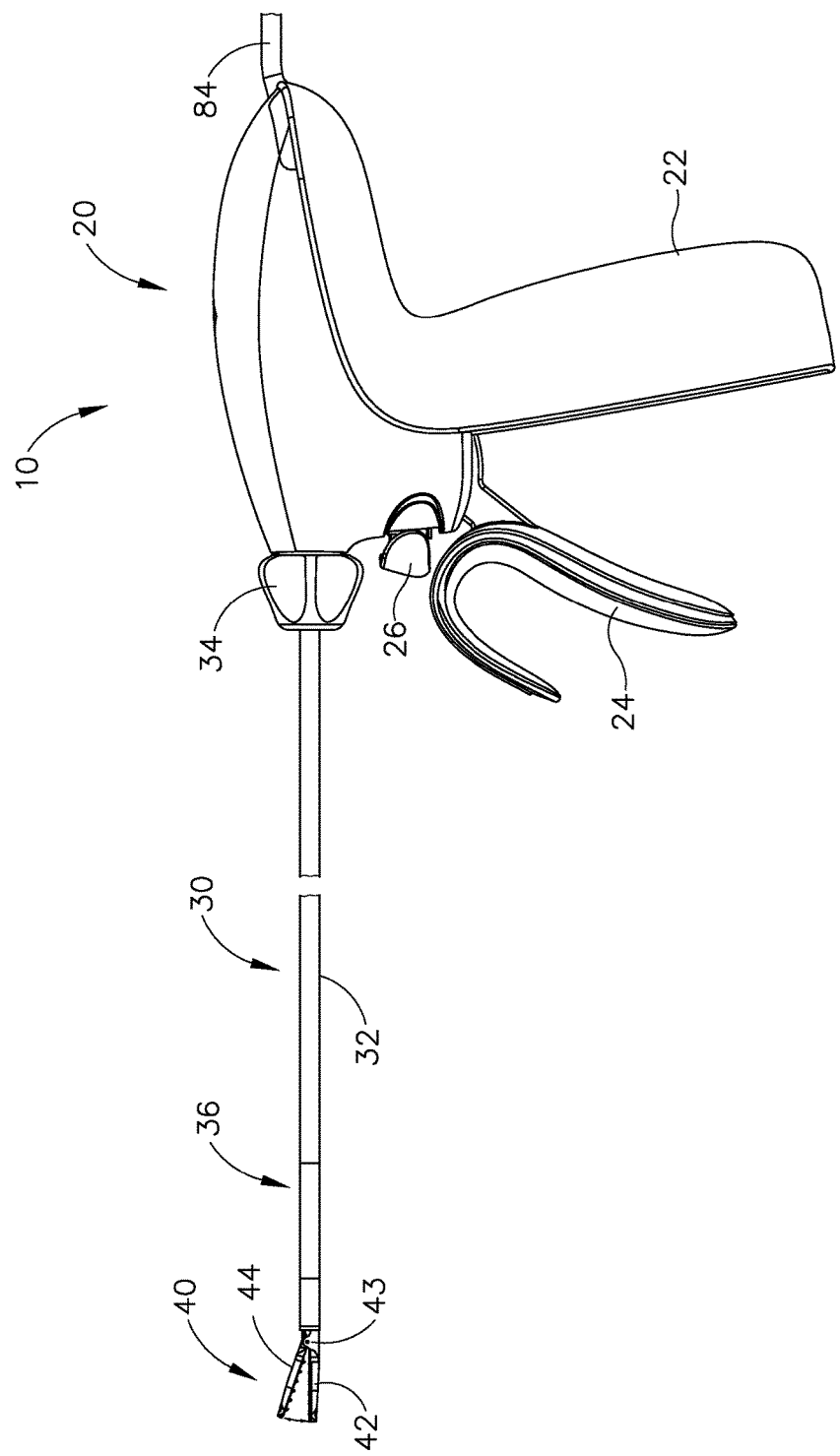
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Device with Articulation Feature

FIGS. 1-4 show an exemplary electrosurgical instrument (10) that is constructed and operable in accordance with at least some of the teachings of U.S. Pat. Nos. 6,500,176, 7,112,201, 7,125,409, 7,169,146, 7,186,253, 7,189,233, 7,220,951, 7,309,849, 7,311,709, 7,354,440, 7,381,209; U.S. Pub. No. 2011/0087218, issued as U.S. Pat. No. 8,939,974 on Jan. 27, 2015; U.S. Pub. No. 2012/0083783, issued as U.S. Pat. No. 8,888,809 on Nov. 18, 2014; U.S. Pub. No. 2012/0116379, issued as U.S. Pat. No. 9,161,803 on Oct. 20, 2015; U.S. Pub. No. 2012/0078243, issued as U.S. Pat. No. 9,877,720 on Jan. 30, 2018; U.S. Pub. No. 2012/0078247, issued as U.S. Pat. No. 9,402,682 on Aug. 2, 2016; U.S. Pub. No. 2013/0030428, issued as U.S. Pat. No. 9,089,327 on Jul. 28, 2015; and/or U.S. Pub. No. 2013/0023868, issued as U.S. Pat. No. 9,545,253 on Jan. 17, 2017. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), and an activation button (26). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes a rigid outer sheath (32) and an articulation section (36). Articulation section (36) is operable to selectively laterally deflect end effector (40) at various angles relative to the longitudinal axis defined by sheath (32). In some versions, articulation section (36) and/or some other portion of outer sheath (32) includes a flexible outer sheath (e.g., a heat shrink tube, etc.) disposed about its exterior. Articulation section (36) of shaft (30) may take a variety of forms. By way of example only, articulation section (36) may be configured in accordance with one or more teachings of U.S. Pub. No. 2012/0078247, issued as U.S. Pat. No. 9,402,682 on Aug. 2, 2016, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, issued as U.S. Pat. No. 9,220,559 on Dec. 29, 2015, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating articulation section (36) or any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating articulation section (36) or any portion of shaft (30) that is proximal of articulation section (36). Other suitable rotation schemes will be apparent to those of ordinary skill in the art in view of the teachings herein. Of course, rotatable features may simply be omitted if desired.

Although not shown, it should be understood that in some examples instrument (10) may include an articulation control (not shown). In such examples, the articulation control may be operable to selectively control articulation section (36) of shaft (30), to thereby selectively laterally deflect end effector (40) at various angles relative to the longitudinal axis defined by shaft (30). In some examples the articulation control may be in the form of a rotary dial. In other examples, the articulation control may take numerous other forms. By way of example only, some merely illustrative forms that the articulation control and other components of handpiece (20) may take are disclosed in U.S. Pub. No. 2012/0078243, issued as U.S. Pat. No. 9,877,720 on Jan. 30, 2018, the disclosure of which is incorporated by reference herein; in U.S. Pub. No. 2012/0078244, entitled "Control Features for Articulating Surgical Device," published Mar. 29, 2012, now abandoned, the disclosure of which is incorporated by reference herein; and in U.S. Pub. No. 2013/0023868, issued as U.S. Pat. No. 9,545,253 on Jan. 17, 2017, the disclosure of which is incorporated by reference herein. Still other suitable forms that the articulation control may take will be apparent to those of ordinary skill in the art in view of the teachings herein. It should also be understood that some versions of instrument (10) may simply lack the articulation control.

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). Use of the term "pivot" should not be read as necessarily requiring pivotal movement about a fixed axis. In some versions, second jaw (44) pivots about an axis that is defined by a pin (or similar feature) that slides along an elongate slot or channel as second jaw (44) moves toward first jaw (42). In such versions, the pivot axis translates along the path defined by the slot or channel while second jaw (44) simultaneously pivots about that axis. It should be understood that such sliding/translating pivotal movement is encompassed within terms such as "pivot," "pivots," "pivotal," "pivotable," "pivoting," and the like. Of course, some versions may provide pivotal movement of second jaw (44) about an axis that remains fixed and does not translate within a slot or channel, etc.

In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
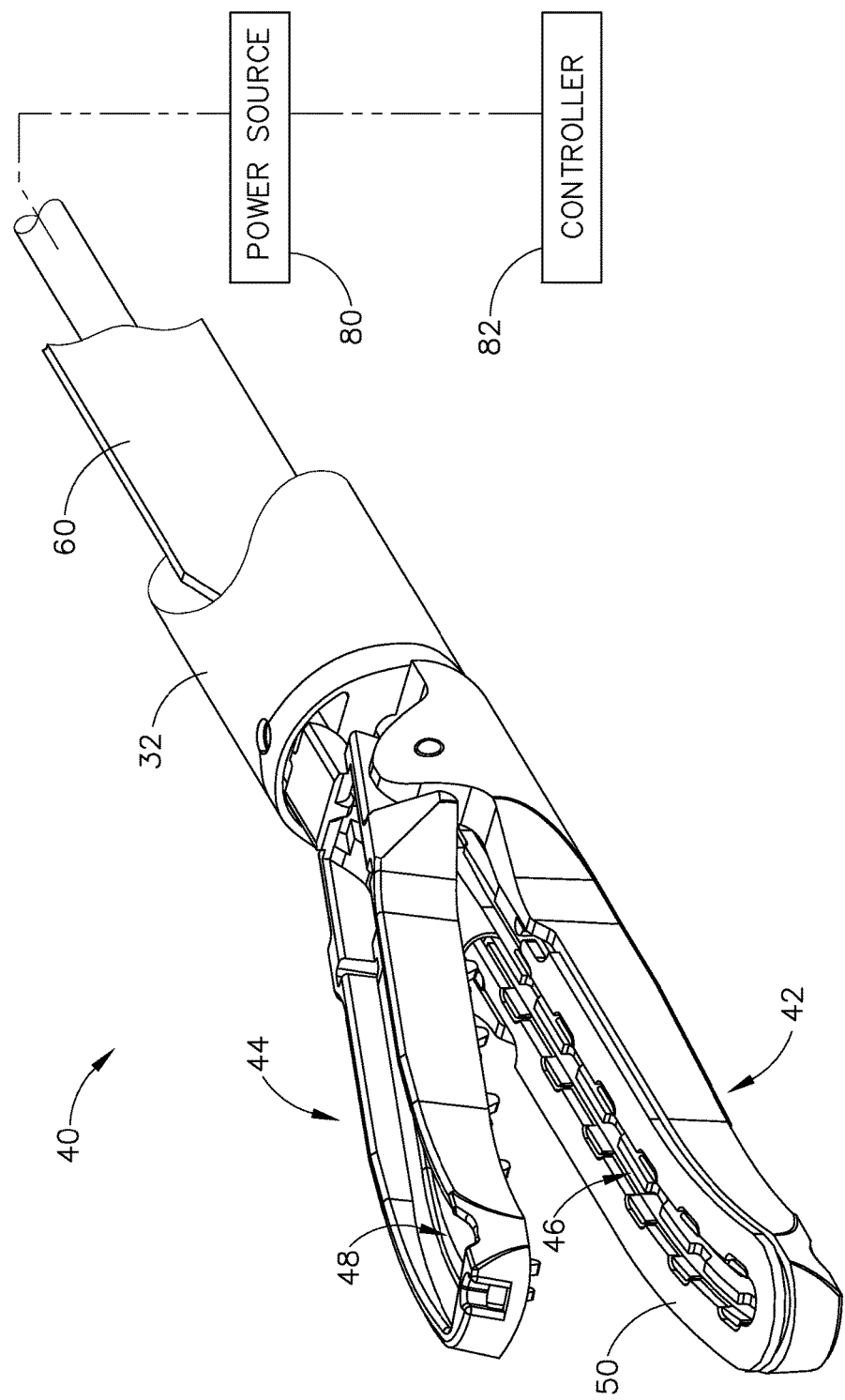
FIG. 2 depicts a perspective view of an end effector of the instrument of FIG. 1, in an open configuration.
Figure 3:
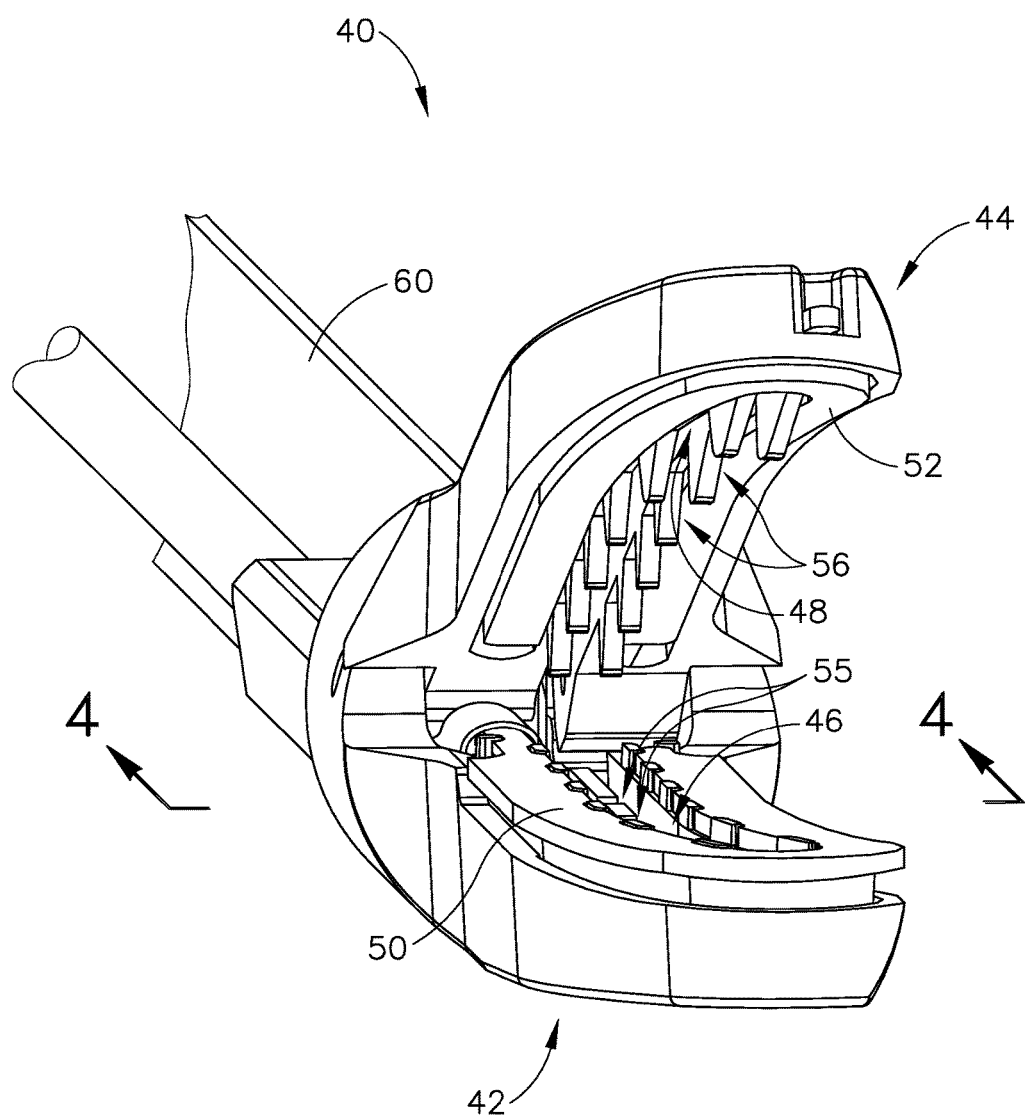
FIG. 3 depicts another perspective view of the end effector of the instrument of FIG. 1, in an open configuration.
Figure 4:
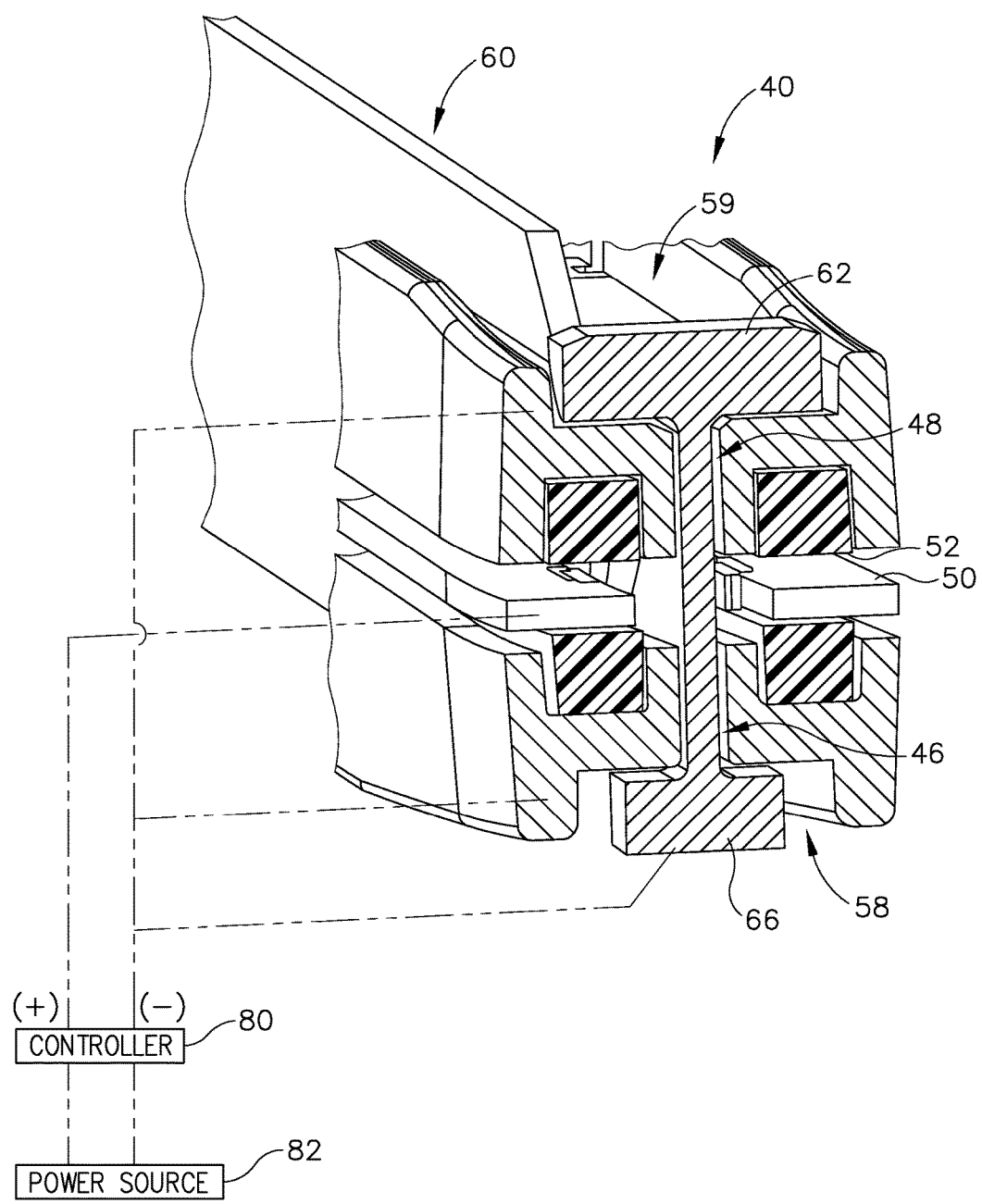
FIG. 4 depicts a cross-sectional end view of the end effector of FIG. 2, taken along line 4-4 of FIG. 3, in a closed configuration and with the firing beam in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode (50); while the underside of second jaw (44) presents a second electrode (52). Electrodes (50, 52) are in communication with an electrical source (80) via one or more conductors (not shown) that extend along the length of shaft (30). These conductors are coupled with electrical source (80) and a controller (82) via a cable (84), which extends proximally from handpiece (20). Electrical source (80) is operable to deliver RF energy to first electrode (50) at an active polarity while second electrode (52) serves as a reference/return passive electrode, such that RF current flows between electrodes (50, 52) and thereby through tissue captured between jaws (42, 44). There are instances where the active signal crosses zero potential that the reference is at the same potential so there is no current flow. In some versions, firing beam (60) serves as an electrical conductor that cooperates with electrodes (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrodes (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrodes (50, 52) may be provided in a variety of alternative locations, configurations, and relationships.

By way of example only, power source (80) and/or controller (82) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, issued as U.S. Pat. No. 9,089,360 on Jul. 28, 2015, the disclosure of which is incorporated by reference herein; U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, issued as U.S. Pat. No. 8,951,248 on Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, issued as U.S. Pat. No. 9,039,695 on May 26, 2015, the disclosure of which is incorporated by reference herein; U.S. Pub. No. 2011/0087215, entitled "Surgical Generator for Ultrasonic and Electrosurgical Devices," published Apr. 14, 2011, issued as U.S. Pat. No. 9,050,093 on Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, issued as U.S. Pat. No. 8,956,349 on Feb. 17, 2015, the disclosure of which is incorporated by reference herein; and/or U.S. Pub. No. 2011/0087217, entitled "Surgical Generator for Ultrasonic and Electrosurgical Devices," published Apr. 14, 2011, issued as U.S. Pat. No. 9,060,776 on Jun. 23, 2015, the disclosure of which is incorporated by reference herein. Other suitable configurations for power source (80) and controller (82) will be apparent to those of ordinary skill in the art in view of the teachings herein.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIGS. 2 and 3 show the upper side of first jaw (42) including a plurality of teeth recesses (55). Correspondingly, the lower side of second jaw (44) includes complementary teeth serrations (56) that nest within recesses (55), to enhance gripping of tissue captured between jaws (42, 44) without necessarily tearing the tissue. In other words, it should be understood that serrations (56) may be generally blunt or otherwise atraumatic. Although FIG. 3 shows first jaw having recesses (55) and second jaw (44) serrations (56) as, it should be understood that recesses (55) and serrations (56) may take any other suitable form or may be simply omitted altogether. It should also be understood that serrations (56) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44). In some versions, serrations (56) are electrically conductive.

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrodes (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (not shown) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrodes (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, the PTC thermistor bodies at end effector (40) may automatically reduce the energy delivery at electrodes (50, 52) as the temperature of the tissue and/or end effector (40) increases, thereby reducing the likelihood of overheating. In some such versions, a PTC thermistor element is in series with power source (80) and electrode (50, 52); and the PTC thermistor provides an increased impedance (reducing flow of current) in response to temperatures exceeding a threshold. Furthermore, it should be understood that electrodes (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

Figure 5:
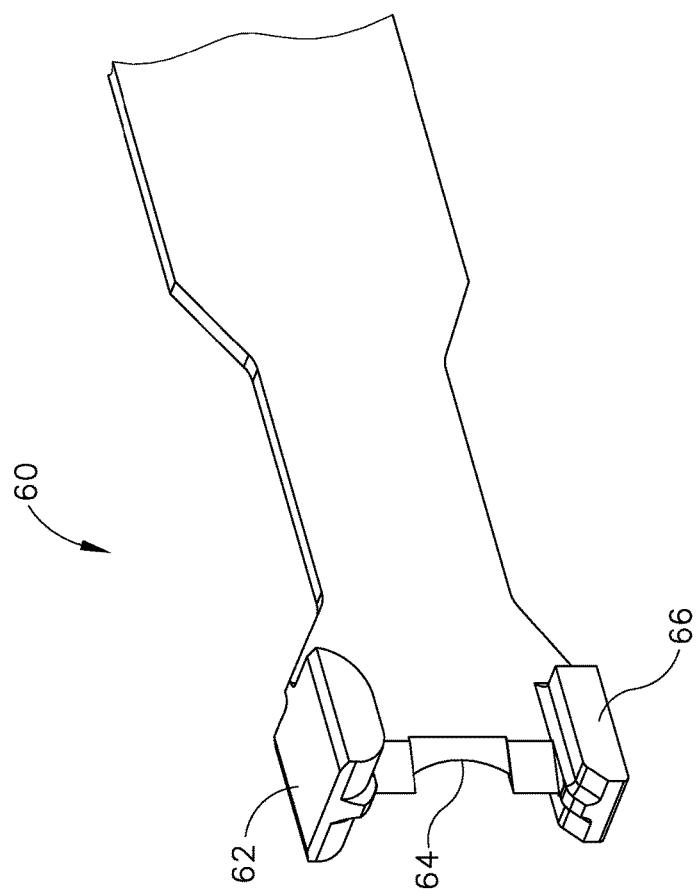
FIG. 5 depicts a partial perspective view of the distal end of the firing beam of the end effector of FIG. 2.

As also seen in FIGS. 2-5, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. In some versions, a proximal end of firing beam (60) is secured to a firing tube or other structure within shaft (30); and the firing tube or other structure extends through the remainder of shaft (30) to handpiece (20) where it is driven by movement of trigger (24). As best seen in FIG. 5, firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode.

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze trigger (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

In some variations, firing beam (60) is modified such that flanges (62, 66) are replaced with pins that extend transversely from the modified firing beam. In other words, one or more upper pins could bear against recess (59) of jaw (44), and one or more lower pins could bear against recess (58) of jaw (42), as the modified firing beam is advanced distally through slots (46, 48). In some such versions, one or more of the pins may be configured to rotate about axes that extend transversely from the modified firing beam, such that the pins roll along recesses (58, 59) as the modified firing beam translates longitudinally through slots (46, 48). The pins may thus provide reduced friction with jaws (42, 44), thereby reducing the force required to translate the modified firing beam. In addition or in the alternative, at least one of the pins may be slidably disposed in a corresponding elongate slot formed through the modified firing beam, such that the pin may translate along a plane defined by the modified firing beam. By way of example only, a modified firing beam may be configured in accordance with at least some of the teachings of U.S. Pub. No. 2012/0083783, issued as U.S. Pat. No. 8,888,809 on Nov. 18, 2014, the disclosure of which is incorporated by reference herein. Other suitable ways in which firing beam (60) may be varied will be apparent to those of ordinary skill in the art in view of the teachings herein.

D. Exemplary Operation

In an exemplary use, end effector (40) is inserted into a patient via a trocar. Articulation section (36) is substantially straight when end effector (40) and part of shaft (30) are inserted through the trocar. The articulation control, if equipped, may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (44) toward jaw (42) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, help keep jaws (42, 44) in a closed and tightly clamping position. In particular, flanges (62, 66) help maintain a significantly compressive force between jaws (42, 44). With severed tissue layer portions being compressed between jaws (42, 44), bipolar RF energy is applied to the tissue through electrodes (50, 52) by the user depressing activation button (26). Thus, a bipolar RF current flows through the compressed regions of severed tissue layer portions. The bipolar RF energy delivered by power source (80) ultimately thermally welds the tissue layer portions on one side of firing beam (60) together and the tissue layer portions on the other side of firing beam (60) together.

In certain circumstances, the heat generated by activated electrodes (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrodes (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrodes (50, 52). Other suitable ways in which instrument (10) may be operable and operated will be apparent to those of ordinary skill in the art in view of the teachings herein.

II. Exemplary End Effector with Removable Electrode

In some instances, certain components of instrument (10) may be reusable while other portions of instrument (10) may be disposable. Furthermore, in instances where parts are reused, some of those parts may be prone to buildup of coagulated blood, tissue, fluids, and/or other substances that may not be easily removed from those portions of instrument (10). It may therefore be desirable to incorporate features into instrument (10) to make instrument (10) readily cleanable, particularly with respect to parts that are reusable. Various examples of how instrument (10) may be configured for ease of cleaning will be described in greater detail below; while other examples will be apparent to those of ordinary skill in the art in view to the teachings herein.

Figure 6:
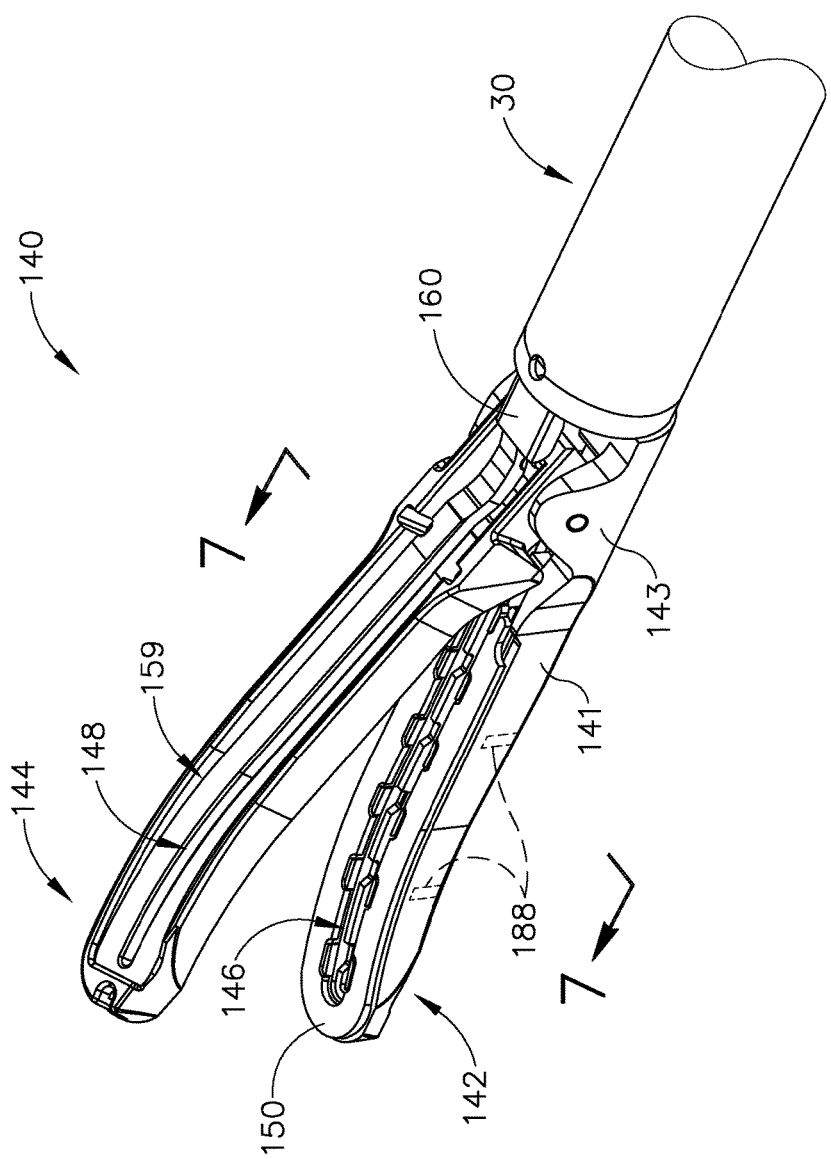
FIG. 6 depicts a perspective view of an exemplary alternative end effector suitable for incorporation in the instrument of FIG. 1.

FIG. 6 shows an exemplary alternative end effector (140) that may be readily incorporated into instrument (10) described above. In particular, end effector (140) is attachable to a distal end of shaft (30) of instrument (10). End effector (140) is substantially the same as end effector (40) described above, except for as otherwise provided herein. For instance, end effector (140) comprises a first jaw (142) and a second jaw (144) that is pivotable relative to the substantially fixed first jaw (142) about a pivotal coupling (143). Also similarly to end effector (40), end effector (140) is configured to actuate to a closed configuration by advancing a firing beam (160) distally through corresponding slots (146, 148) and recesses (158, 159) in first jaw (142) and second jaw (144), respectively. Additionally, first jaw (142) and second jaw (144) include electrodes (150, 152) that are configured to apply RF energy to tissue and thereby seal tissue as described above with respect to electrodes (50, 52).

Figure 7:
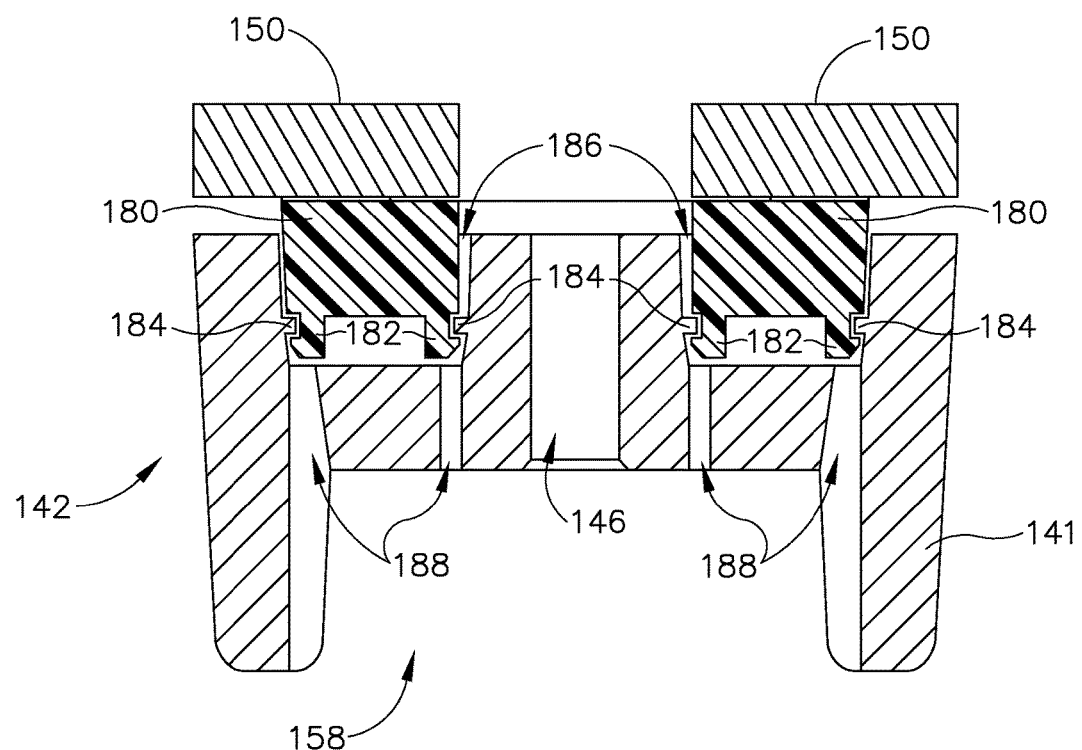
FIG. 7 depicts a front cross-sectional view of a first jaw of the end effector of FIG. 6, the cross-section taken along line 7-7 of FIG. 6.

Generally, end effector (140) varies from end effector (40) in that end effector (140) includes features that permit the removal of electrode (150). As can be seen in FIG. 7, electrode (150) is unitarily attached to an insulating member (180). In the present example, insulating member (180) is overmolded onto electrode (150). In other, examples insulating member (180) may be attached to electrode (150) by any suitable means such as adhesive bonding, welding, or any other suitable means of attachment. Insulating member (180) includes two integral resilient tabs (182) protruding from the bottom of insulating member (180). Resilient tabs (182) are configured to engage two corresponding protrusions (184) that protrude from each side of an insulator recess (186) in first jaw (142). Thus, the assembly formed by electrode (150) and insulating member (180) is removably secured to the body (141) of first jaw (142) through a snap fit. In the present example, insulating member (180) is comprised of an electrically insulating resilient yet semi-rigid material such as rubber, polyethylene, polypropylene, polyurethane, or the like. Also in the present example, resilient tabs (182) extend along the entire longitudinal length of insulating member (180). Similarly, protrusions (184) extend along the entire longitudinal length of recess (186). In other examples, either resilient tabs (182) or protrusions (184) may extend along only discrete portions of insulating member (180) and recess (186), respectively.

As best seen in FIG. 7, body (141) of first jaw (142) of the present example also includes four access channels (188). Access channels (188) extend downwardly from insulator recess (186) to recess (158). In particular, each access channel (188) is positioned to correspond to the position of at least a portion of each resilient tab (182) and protrusion (184) interface. Additionally, recess (158) extends transversely across first jaw (142) for a distance that is greater relative to the same distance with respect to recess (58) described above. This increased transverse extension of recess (158) permits each access channel (188) to intersect with recess (158). As will be described in greater detail below, access channels (188) and recess (158) are together configured to receive an electrode removal tool (190) that may engage resilient tabs (182) to permit removal of the assembly formed by electrode (150) and insulating member (180).

Figure 8:
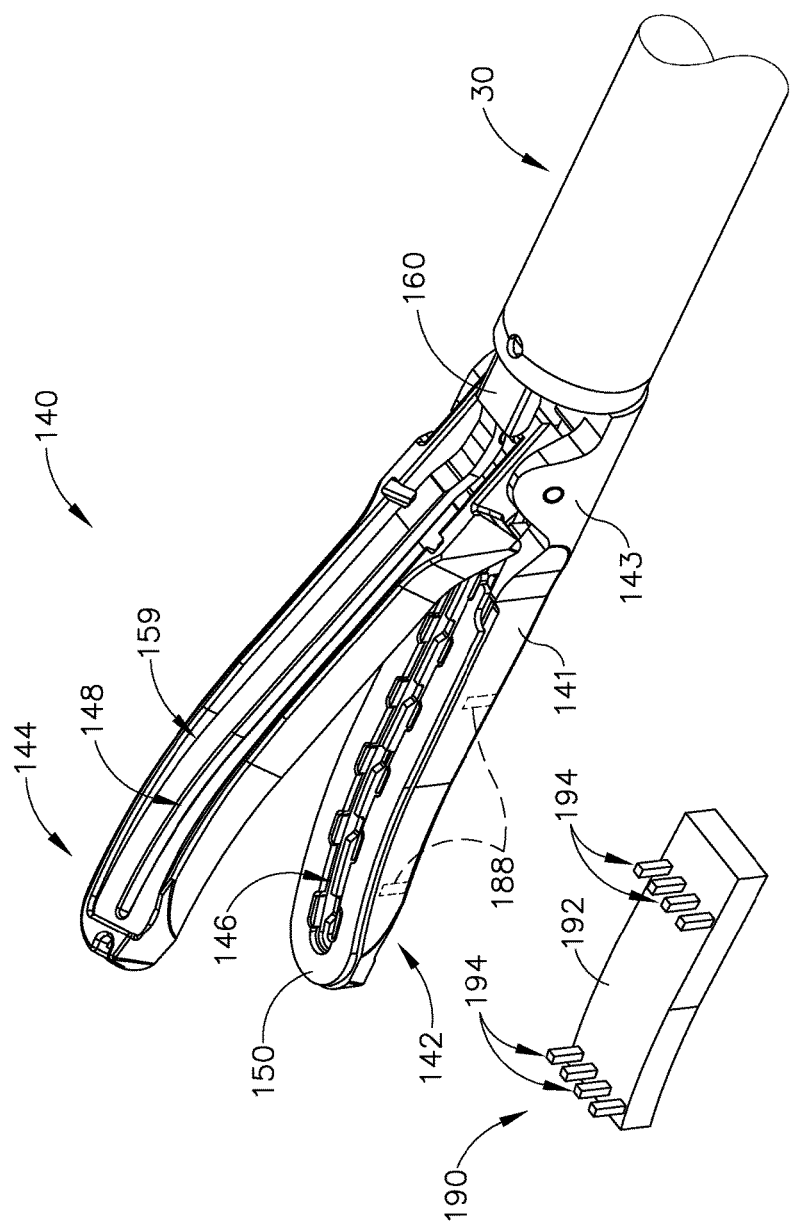
FIG. 8 depicts another perspective view of the end effector of FIG. 6 prior to an electrode removal tool being inserted into the end effector.

FIG. 8 shows electrode removal tool (190) prior to insertion into first jaw (142). As can be seen, electrode removal tool (190) comprises a body (192) and two sets of four actuation members (194). Body (192) is generally rectangular in shape and is configured to mate with recess (158) of first jaw (142). Actuation members (194) extend upwardly from a top surface of body (192) in the form of prongs with a shape corresponding to each access channel (188). As can best be seen in FIG. 10, actuation members (194) include angled ends (196) on the top of each actuation member (194). As will be described in greater detail below, angled ends (196) are generally configured to engage resilient tabs (182) to disengage resilient tabs (182) from protrusions (184).

Figure 10:
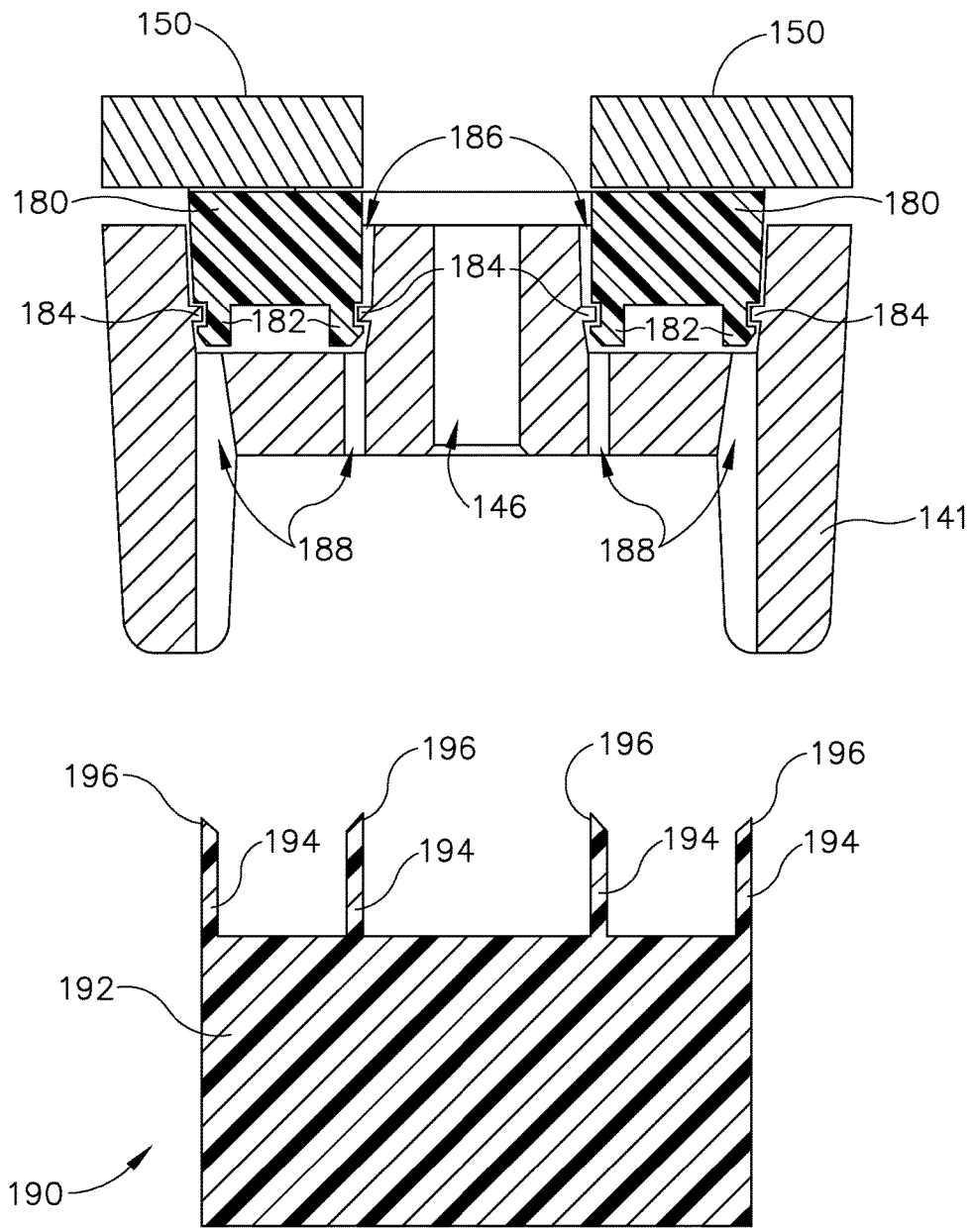
FIG. 10 depicts a front cross-sectional view of the end effector of FIG. 6 prior to the electrode removal tool being inserted into the end effector.

In an exemplary use, electrode removal tool (190) is initially aligned with recess (158) of first jaw (142), as can be seen in FIGS. 8 and 10. Once aligned, a user may move electrode removal tool (190) upwardly and into recess (158) of first jaw (142). As electrode removal tool (190) is moved upwardly, actuation members (194) may enter a corresponding access channel (188). As actuation members (194) advance through access channels (188), angled ends (196) approach resilient tabs (182) until angled ends (196) contact resilient tabs (182).

Figure 9:
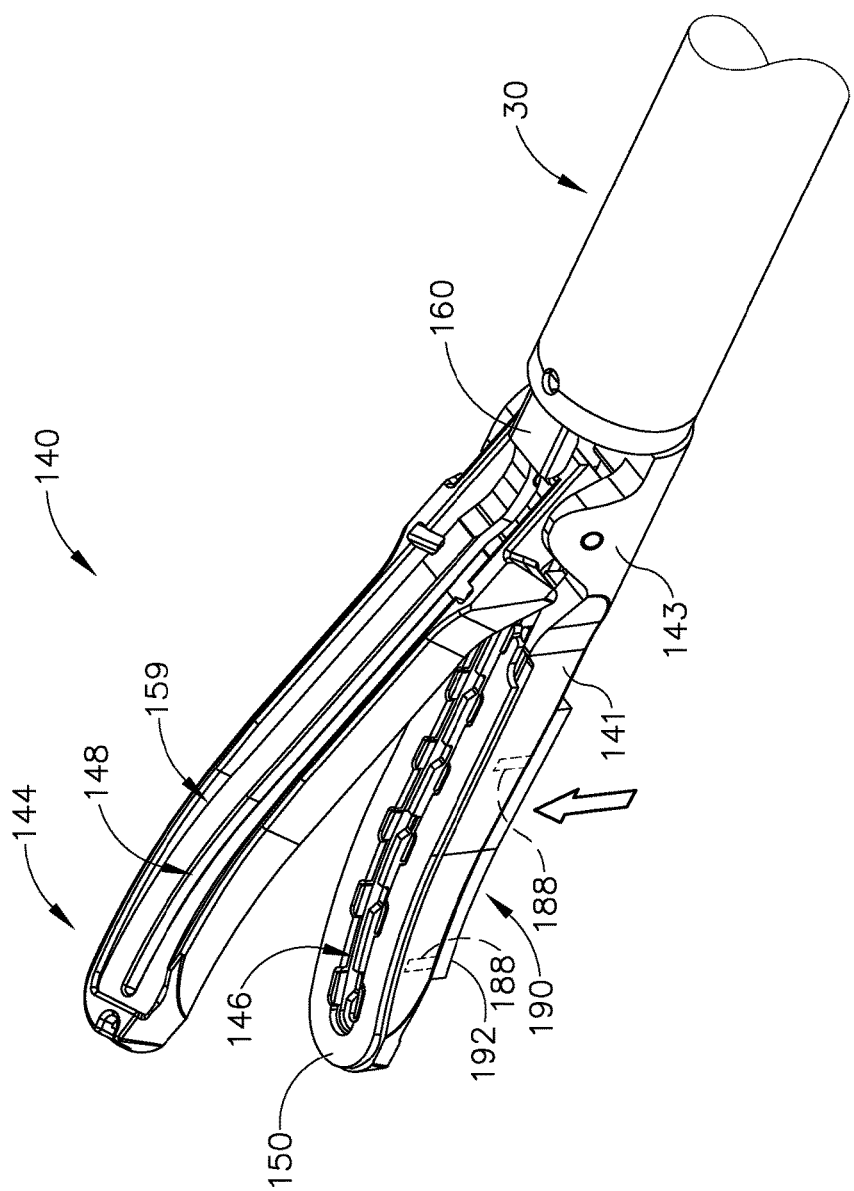
FIG. 9 depicts yet another perspective view of the end effector of FIG. 6, with the electrode removal tool inserted into the end effector.
Figure 11:
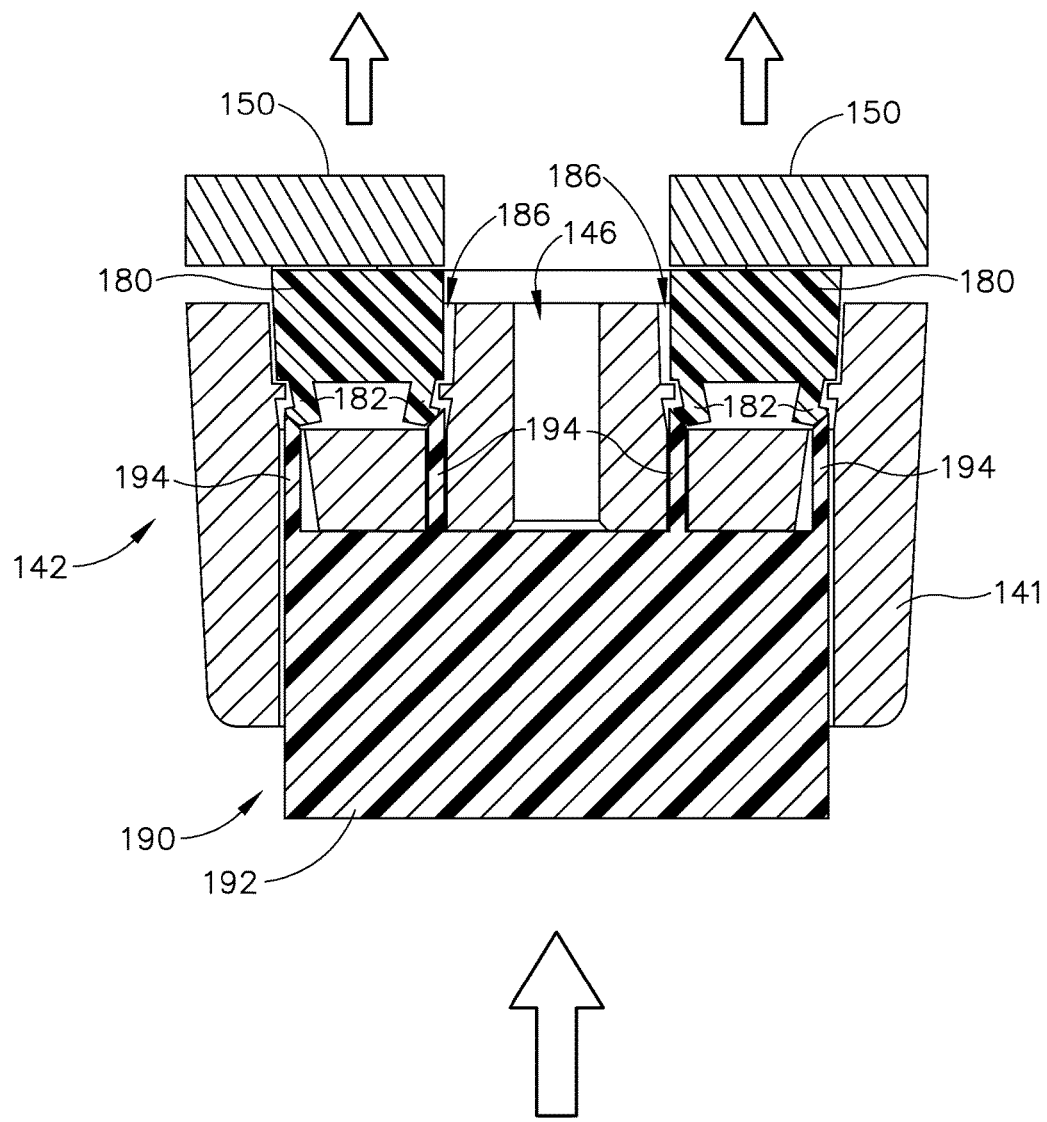
FIG. 11 depicts a front cross-sectional view of the end effector of FIG. 6, with the electrode removal tool being inserted into the end effector.

Once angled ends (196) contact resilient tabs (182), a user may be required to exert additional force on electrode removal tool (190). Such a force may be required to overcome the resilient bias of resilient tabs (182) that maintains engagement between resilient tabs (182) and protrusions (184). Regardless of the force required, a user may move electrode removal tool (190) completely into recess (158) of first jaw (142), as seen in FIGS. 9 and 11. Such movement causes angled ends (196) to fully engage resilient tabs (182). The complementarily angled configurations of angled ends (196) and tabs (182) provides a camming action as actuation members (194) are driven into tabs (182), causing tabs (182) to deflect away from protrusions (184). Actuation members (194) thus disengage resilient tabs (182) from protrusions (184) and force insulating member (180) upwardly relative to insulator recess (186). With resilient tabs (182) fully disengaged from protrusions (184), a user may grasp electrode (150) and/or insulating member (180) and remove the assembly formed by electrode (150) and insulating member (180) from first arm (142).

Figure 12:
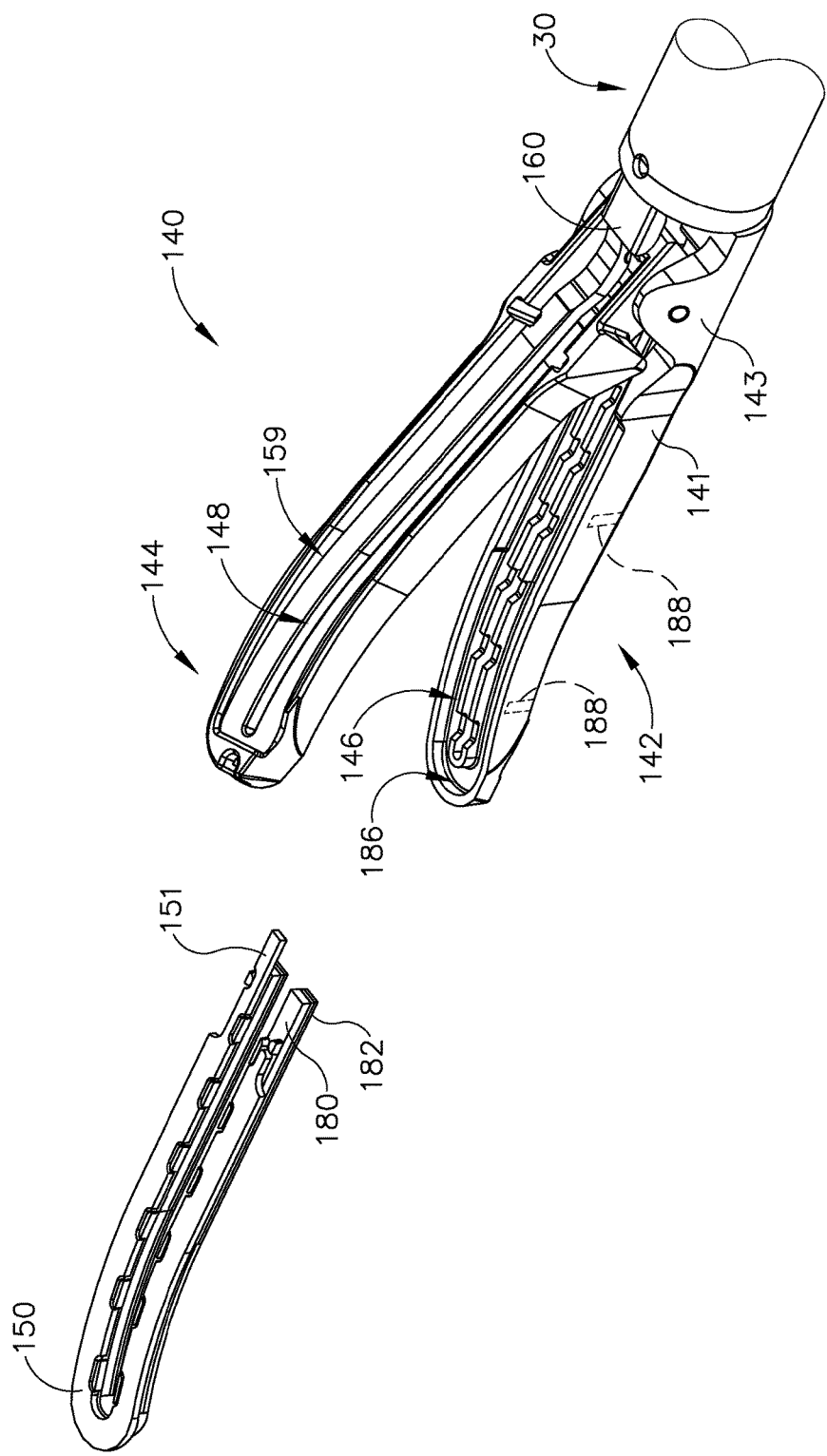
FIG. 12 depicts still another perspective view of the end effector of FIG. 6, with an electrode and insulating member removed.

FIG. 12 shows electrode (150) and insulating member (180) after a user has removed electrode (150) and insulating member (180) from end effector (140). As can be seen, electrode (150) includes a coupling member (151). Coupling member (151) is configured to electrically couple electrode (150) to shaft (30) such that electrical source (80) may communicate electrical energy to electrode (150). It should be understood that in some examples shaft (30) may include a mill-max connector or other similar coupling to permit a user to easily connect and disconnect electrode (150) with shaft (30). In such examples, the mill-max connector may include one or more sensors that are operable to provide a signal to controller (82) to indicate that electrode (150) is properly connected with shaft (30). Accordingly, in such examples that particular shape of coupling member (151) may be varied to accommodate such a connector in of shaft (30). Similarly, in other examples, other portions of first jaw (142) may include one or more sensors that are operable to provide a signal to controller (82) to indicate that electrode (150) is properly seated in first jaw (142). Such sensors may include any suitable sensor such as electromechanical sensors/switches, magnetic proximity sensors, light sensors, RFID sensors, etc.

With electrode (150) and insulating member (180) decoupled from end effector (140), a user may then clean end effector (140), and electrode (150) and insulating member (180). After these components are cleaned, electrode (150) and insulating member (180) may be re-coupled with first jaw (142) by pressing electrode (150) and insulating member (180) into first jaw (142) until tabs (182) achieve a snap fit with protrusions (184). In some examples, only the remaining portion of end effector (140) is cleaned while electrode (150) and insulating member (180) are discarded for a new electrode (150) and insulating member (180). Yet in other examples, end effector (140), electrode (150) and insulation member (180) may be discarded for entirely new components. Although not shown, it should be understood that in some examples other components may be removable in addition to electrode (150) and insulating member (180). For instance, in some examples, firing beam (60) may be removable in addition to electrode (150) and insulating member (180). Similarly, electrode (152) may be removable from second jaw (144) in some versions, in a manner similar to that through which electrode (150) is removable from first jaw (142). Yet in other examples, any other component of end effector (140), including end effector itself (140), as will be apparent to those of ordinary skill in the art in view of the teachings herein.

Figure 13:
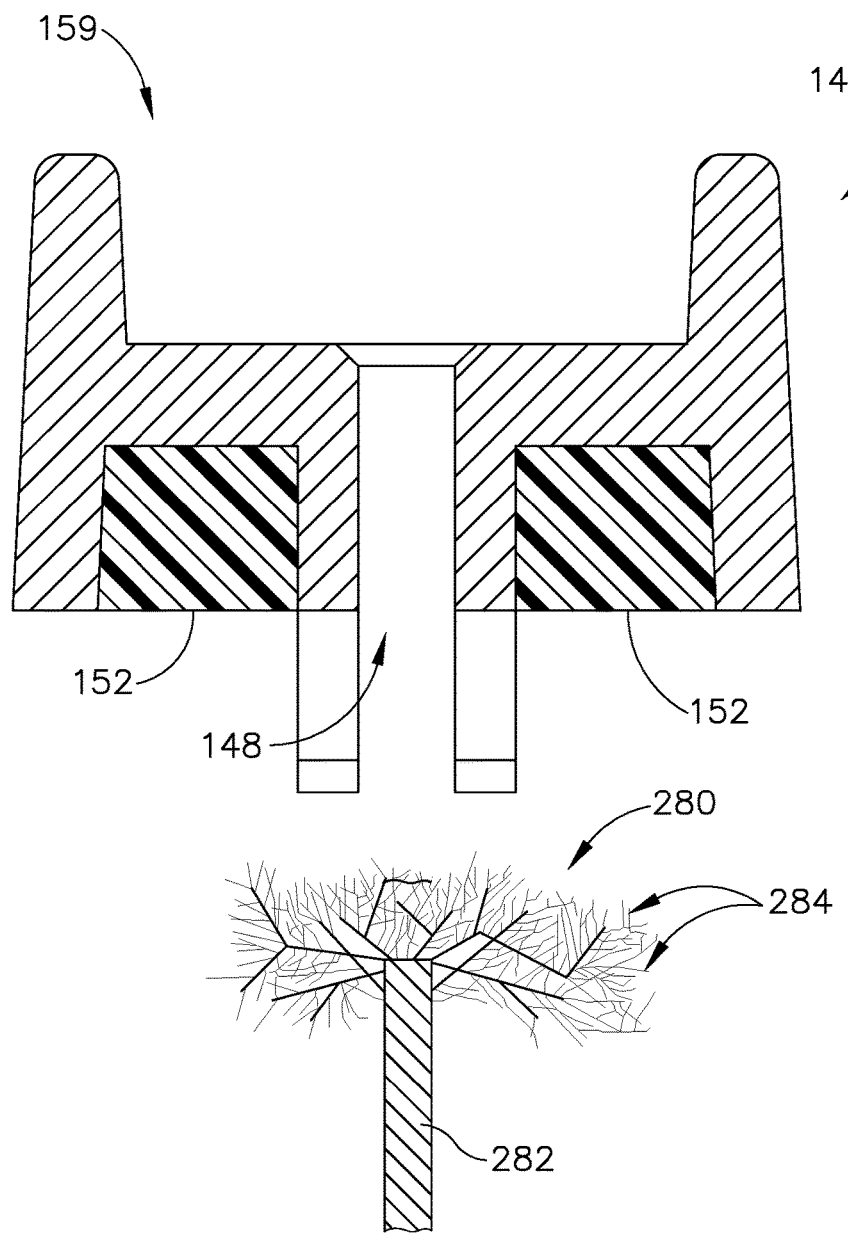
FIG. 13 depicts a front cross-sectional view of a second jaw of the end effector of FIG. 6 prior to a cleaning brush being inserted into the second jaw.

FIG. 13 shows an exemplary cleaning tool (280) that may be used with end effector (140). In particular, cleaning tool (140) comprises a shaft (282) and a plurality of bristles (284). Shaft (282) is an elongate rigid shaft that is configured to be grasped by a user such that a user may move shaft (282) into slot (148) of second jaw (144), as will be described in greater detail below.

Bristles (284) extend outwardly from shaft (282). Although each individual bristle (284) is shown as being randomly oriented away from shaft (282), bristles (284) as a whole are oriented to form a t-shape with shaft (282) that may complement the shape of recess (159) in second jaw (144). Bristles (284) of the present example are comprised of metal wires of varying thickness. In other examples, bristles (284) may be comprised of any other suitable material such as nylon, vinyl, rubber, hair, and/or any other suitable material. Additionally, while bristles (284) are shown as varying in thickness, it should be understood that bristles (284) may be of uniform thickness.

Figure 14:
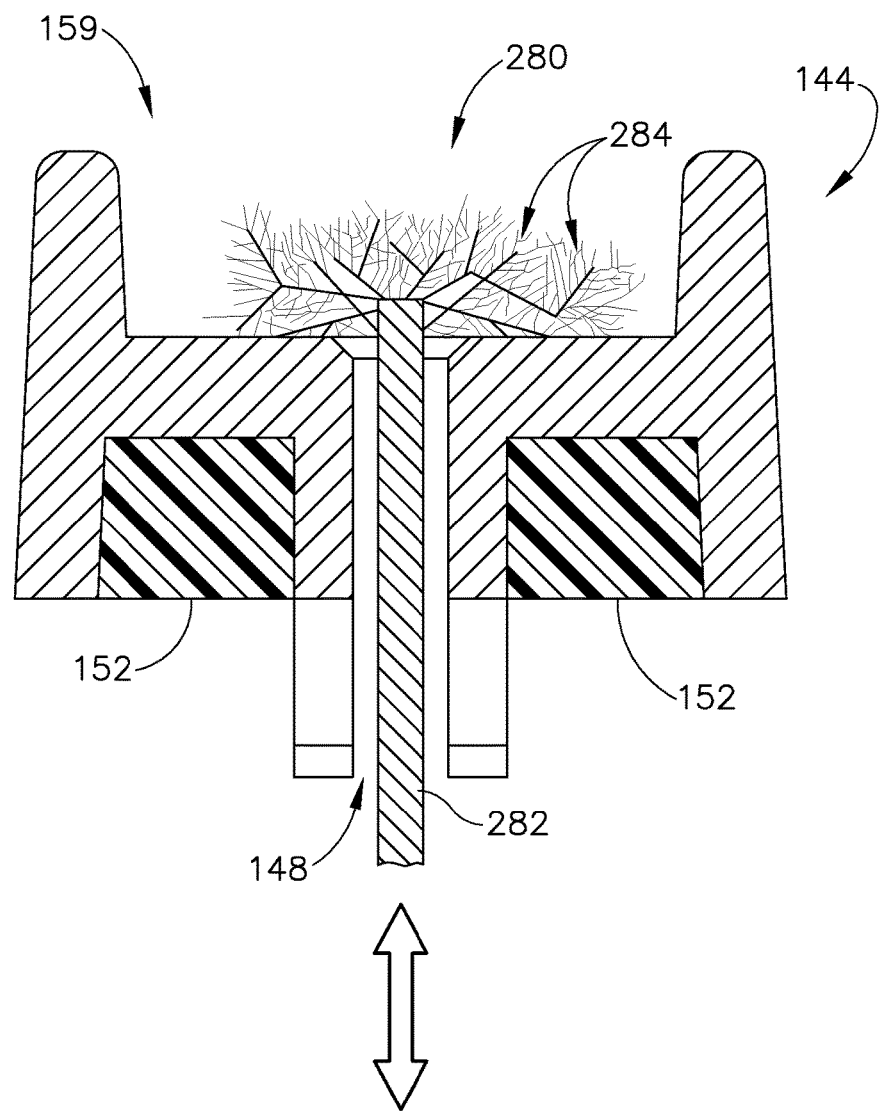
FIG. 14 depicts another front cross-sectional view of the second jaw of FIG. 13, with the cleaning brush inserted into the second jaw.

An exemplary use of tool (280) is shown in FIGS. 13 and 14. In particular, a user may initially position tool (280) below second jaw (144) (e.g., while end effector (140) is in the open configuration). A user may then move tool (280) upwardly to force bristles (284) through slot (148) and into recess (159). Bristles (284) are disposed within recess (159), a user may reciprocate tool (280) along the longitudinal axis of second jaw (144) to clean recess (159). Additionally, a user may reciprocate bristles (284) in and out of slot (148) while reciprocating along the length of end effector (140) to clean slot (148). It should be understood that although tool (280) is shown as being usable with second jaw (144), tool (280) may similarly be used to clean first jaw (142). It should also be understood that saline and/or some other fluid may be used in combination with tool (280) to assist in flushing debris that is brushed from second jaw (144) with tool (280).

III. Exemplary Removable End Effector with Lip Seal

In some instances, instrument (10) may comprise a disposable end effector similar to end effector (40) described above. In particular, such an end effector may be removable from instrument (10) after use such that it may be replaced with an entirely new end effector. In such examples, it may be desirable to keep fluids and or tissues out of other components of instrument (10) to make the other components readily cleanable for reuse. Various examples of how instrument (10) may include such a removable end effector will be described in greater detail below; while other examples will be apparent to those of ordinary skill in the art in view to the teachings herein.

Figure 15:
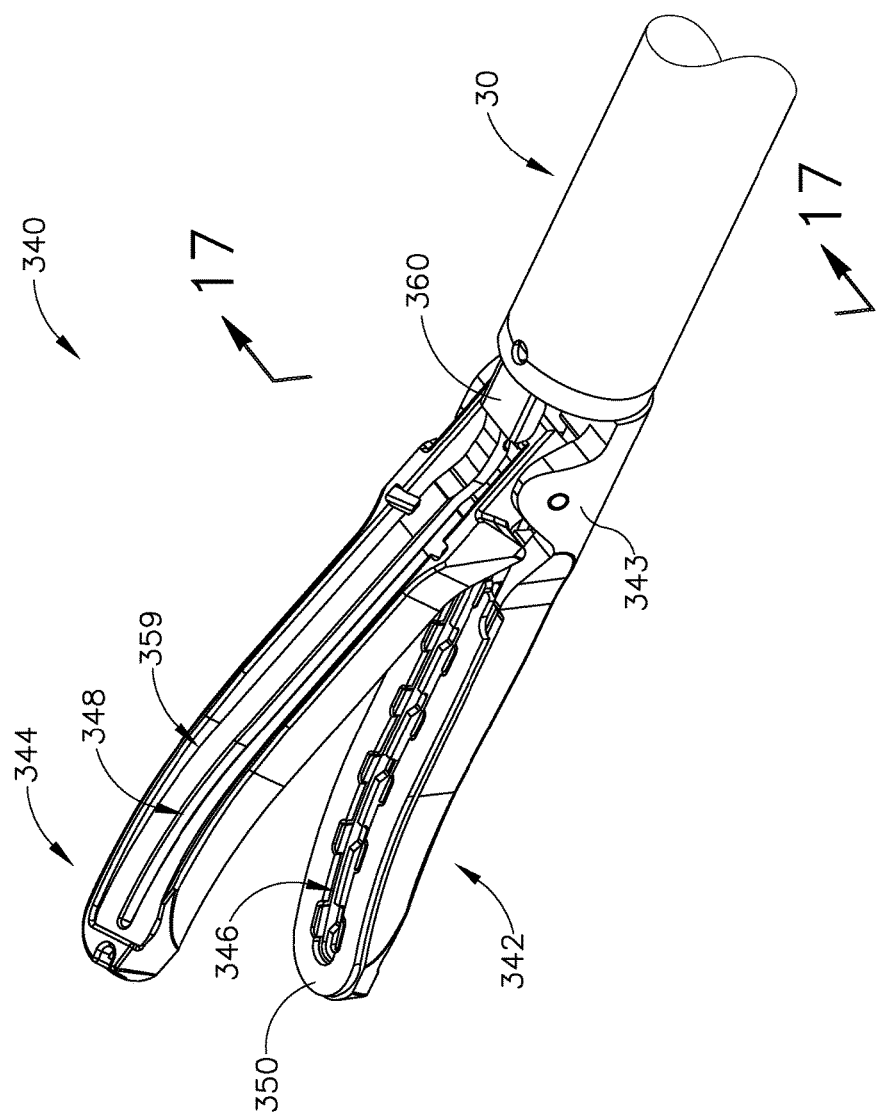
FIG. 15 depicts a perspective view of an exemplary alternative end effector suitable for incorporation in the instrument of FIG. 1.
Figure 16:
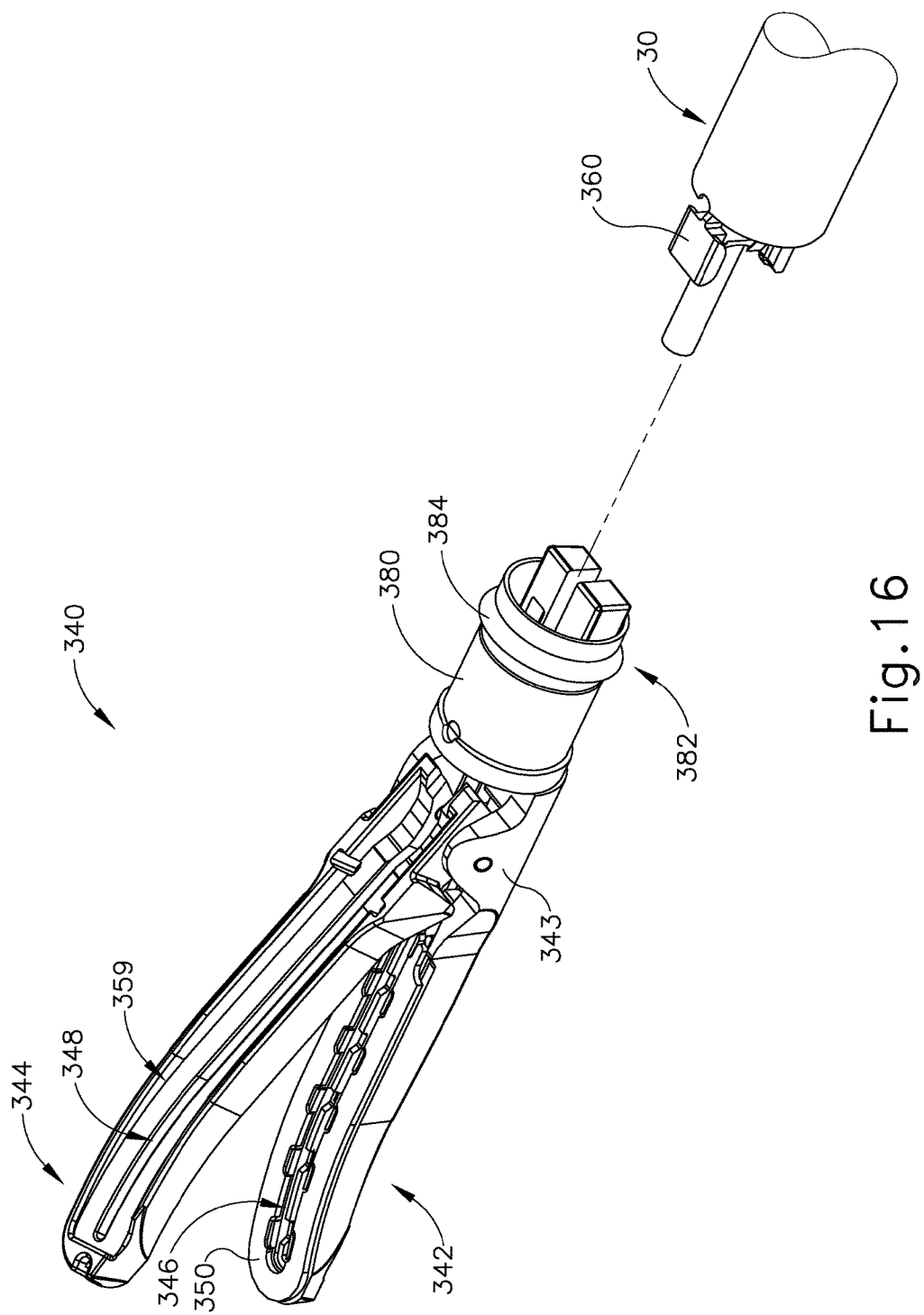
FIG. 16 depicts a partially exploded view of the end effector of FIG. 15, with the end effector separated from a shaft.
Figure 17:
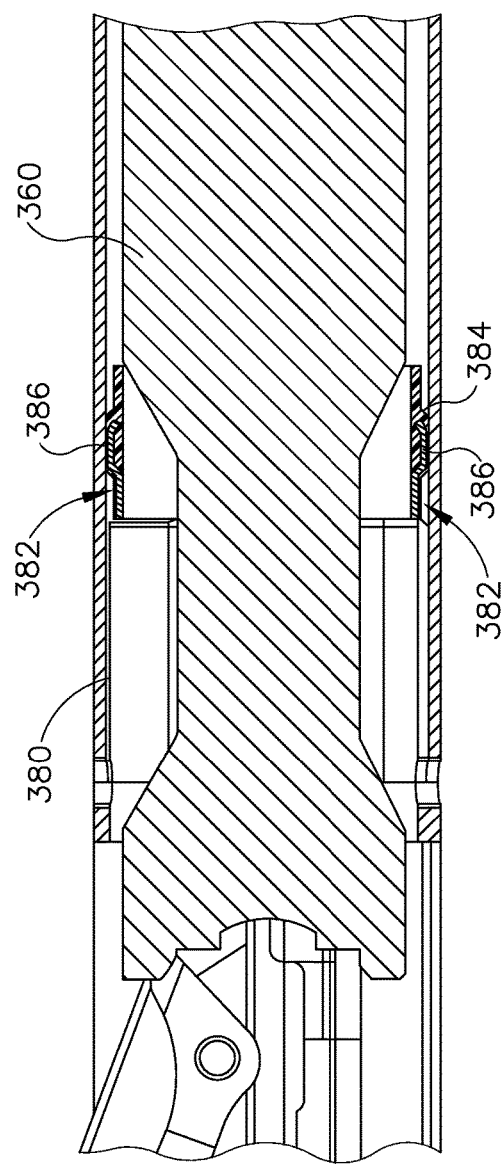
FIG. 17 depicts a front cross-sectional view of the end effector of FIG. 15, with the cross-section taken along line 17-17 of FIG. 15.

FIGS. 15-17 show an exemplary alternative end effector (340) that may be readily incorporated into instrument (10) described above. In particular, end effector (340) is attachable to a distal end of shaft (30) of instrument (10). End effector (340) is substantially the same as end effector (40) described above, except for as otherwise provided herein. For instance, end effector (340) comprises a first jaw (342) and a second jaw (344) that is pivotable relative to the substantially fixed first jaw (342) about a pivotal coupling (343). Also similarly to end effector (40), end effector (340) is configured to actuate by advancing a firing beam (360) distally through corresponding slots (346, 348) and recesses (358, 359) in first jaw (342) and second jaw (344), respectively. Additionally, first jaw (342) and second jaw (344) include electrodes (350) that are configured to seal tissue as described above with respect to electrodes (50, 52).

As can be seen in FIG. 16, end effector (340) generally varies from end effector (40) in that end effector (340) is removable from shaft (30). In particular, end effector (340) includes an attachment collar (380) that is insertable into shaft (30). Collar (380) includes a seal (382) that sealably engages an interior portion of shaft (30). Although not shown, it should be understood that collar (380) may also include attachment or locking features that may selectively lock end effector (340) to shaft (30). By way of example only, suitable attachment or locking features may include resilient members, mechanical locking mechanisms, bayonet mount features, threading, etc. In other examples, the outer diameter of collar (380) may merely be oversized relative to the inner diameter of collar (30) such that end effector (340) is secured to shaft (30) by a compression fit. It should be understood that in addition to locking features, collar (380) and/or shaft (30) may also include one or more sensors configured to sense whether end effector (340) is properly seated within shaft (30). Such sensors may include electromechanical sensors and/or switches that may be configured to detect the positioning of collar (380) relative to shaft (30).

Seal (382) includes an outwardly extending protrusion (384) that sealably engages the interior portion of shaft (30) as described above. Protrusion (384) of the present example is configured as a spring loaded lip seal. In particular, as can be seen in FIG. 17, protrusion (384) is formed by a resilient member (386) including a curved proximal end that extends through seal (382). Resilient member (386) is comprised of a relatively rigid, yet resiliently deformable material. To form the remainder of seal (382), resilient member (386) is coated or overmolded with a relatively soft material such as rubber.

In an exemplary use, seal (382) is initially positioned in shaft (30). When seal (382) is positioned in shaft (30), resilient member (386) urges protrusion (384) outwardly into contact with the inner diameter of shaft (30). After a user has used end effector (340) to cut and seal tissue as described above, a user may remove end effector (340) from shaft (30). As end effector (340) is removed from shaft (30), resilient member (386) continues to urge protrusion (384) outwardly to maintain contact between protrusion (384) and the inner diameter of shaft (30). This continued contact between protrusion (384) and shaft (30) permits protrusion (384) to act as a squeegee to remove tissue and fluid from the inner diameter of shaft (30). End effector (340) may then be cleaned and re-coupled with shaft (30). Alternatively, a new end effector (340) may then be coupled with shaft (30).

IV. Exemplary End Effectors with Electrode Seal

Figure 18:
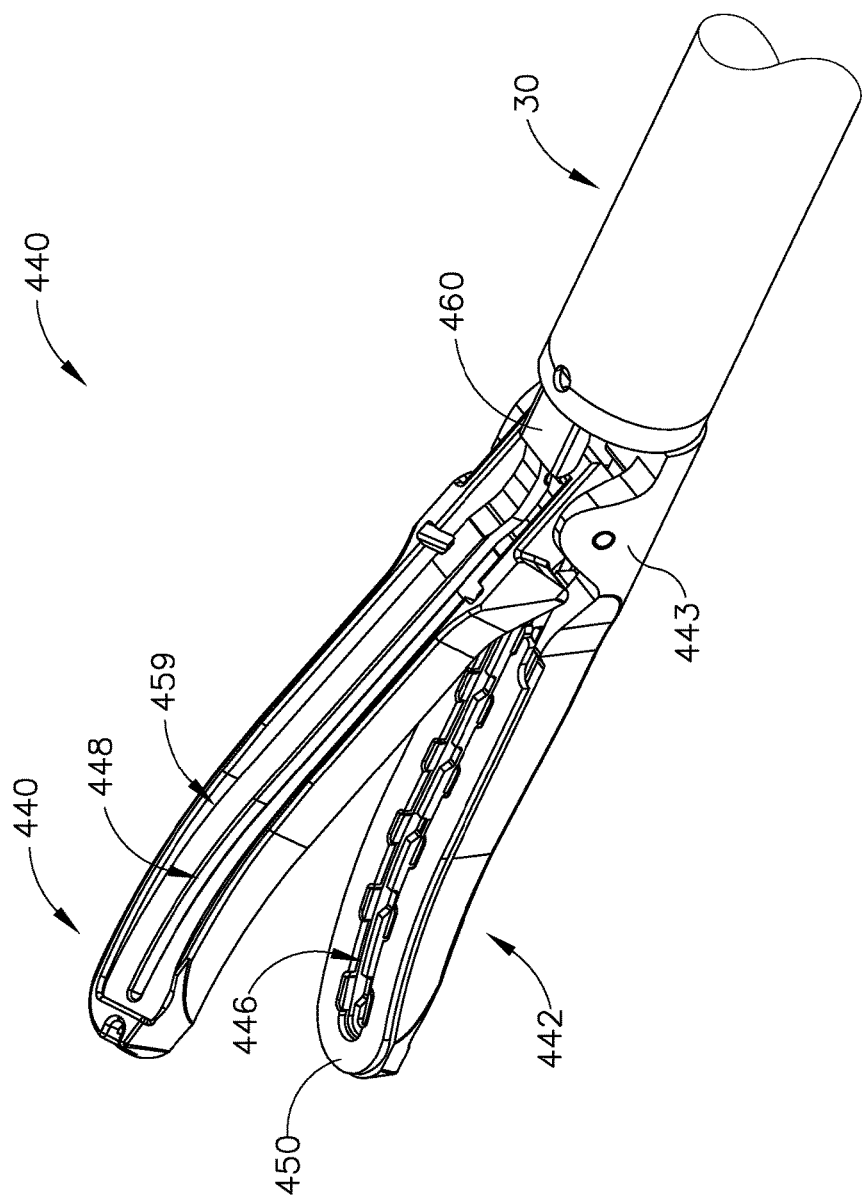
FIG. 18 depicts a perspective view of an exemplary alternative end effector suitable for incorporation in the instrument of FIG. 1.
Figure 19:
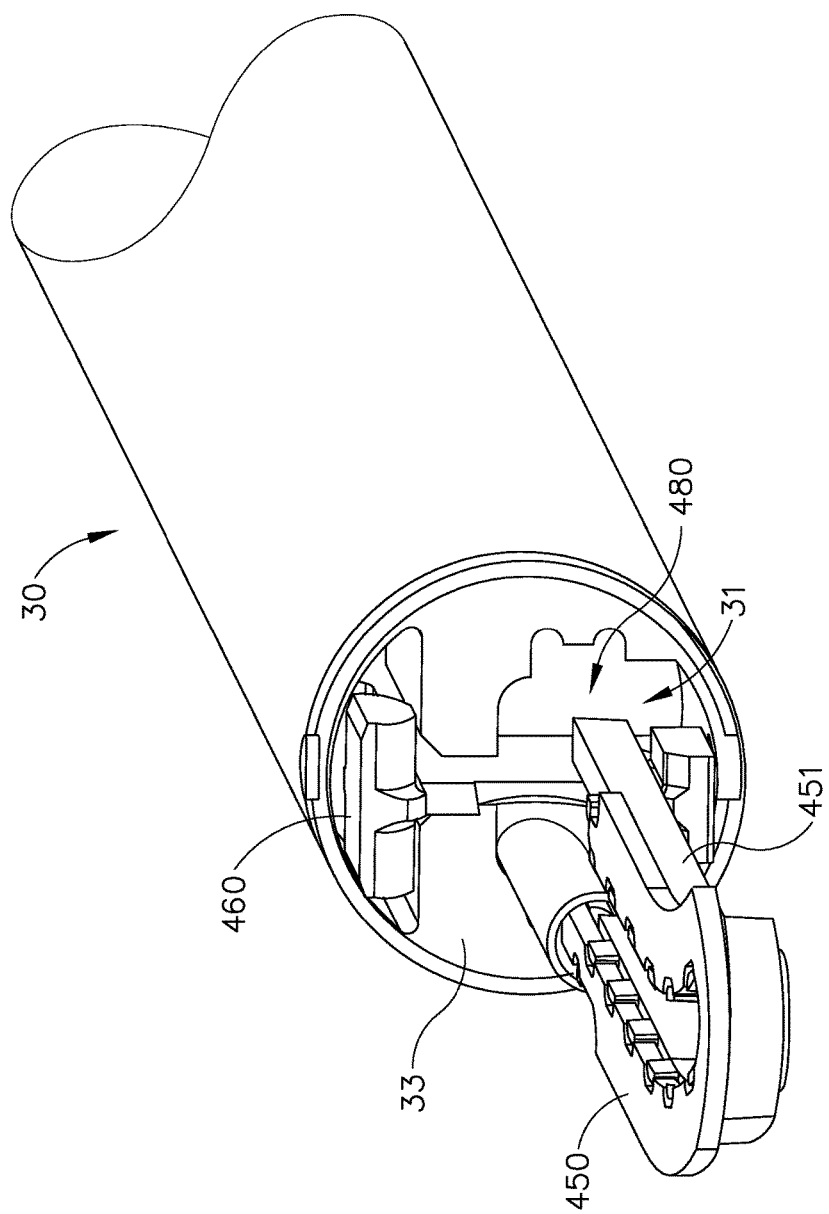
FIG. 19 depicts another perspective view of the end effector of FIG. 18, with a first and second jaw removed.
Figure 20:
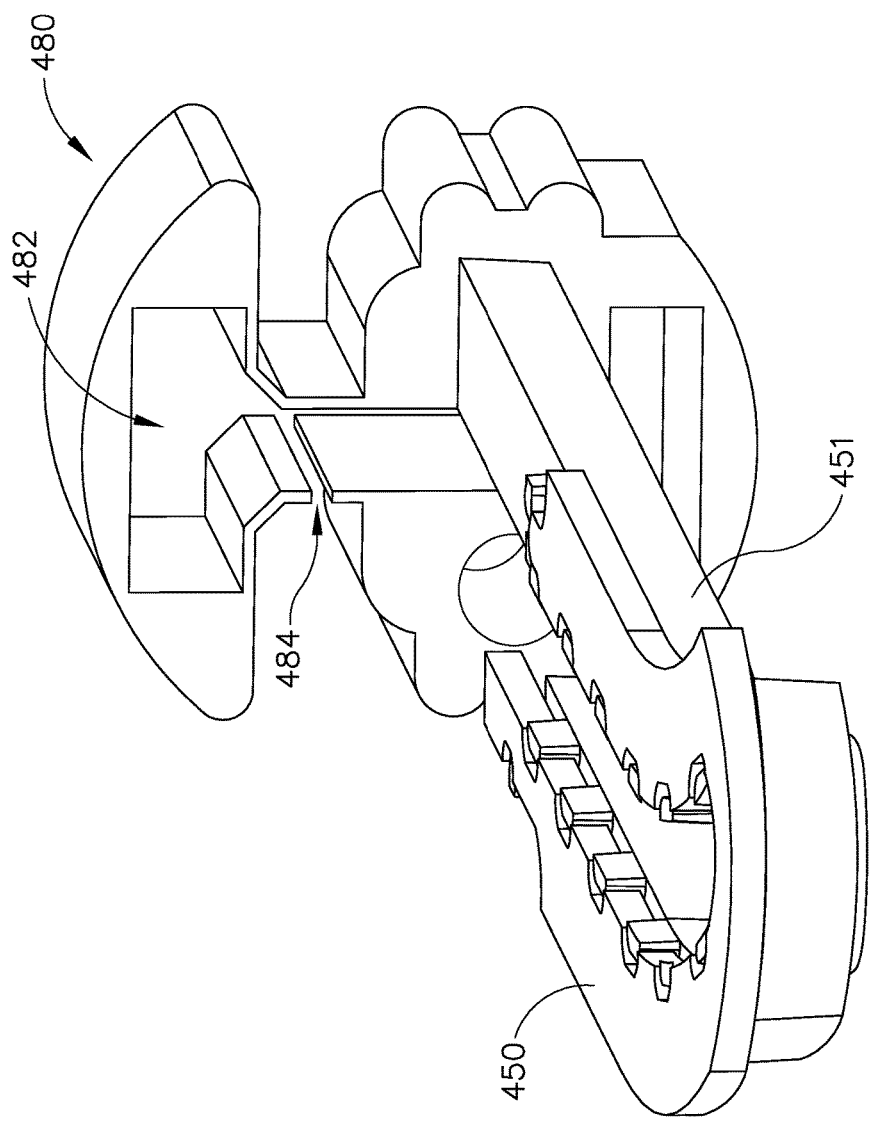
FIG. 20 depicts a perspective view of a seal of the end effector of FIG. 18.

FIGS. 18-20 show an exemplary alternative end effector (440) that may be readily incorporated into instrument (10) described above. In particular, end effector (440) is attachable to a distal end of shaft (30) of instrument (10). End effector (440) is substantially the same as end effector (40) described above, except for as otherwise provided herein. For instance, end effector (440) comprises a first jaw (442) and a second jaw (444) that is pivotable relative to the substantially fixed first jaw (442) about a pivotal coupling (443). Also similarly to end effector (40), end effector (440) is configured to actuate by advancing a firing beam (460) distally through corresponding slots (446, 448) and recesses (458, 459) in first jaw (442) and second jaw (444), respectively. Additionally, first jaw (442) and second jaw (444) include electrodes (450) that are configured to seal tissue as described above with respect to electrodes (50, 52).

Unlike end effector (40), end effector (440) of the present example includes a seal (480) that is configured to seal the interface between shaft (30) and firing beam (460). As can be seen in FIG. 19, which shows end effector (440) with first jaw (442) and second jaw (444) removed, an insulating member (451) that supports electrode (450) is attached to seal (480). Seal (480) is disposed within an aperture (31) in a cap (33) at the distal end of shaft (30) and interfaces with firing beam (460).

As best seen in FIG. 20, seal (480) has a shape corresponding to aperture (31) such that seal (480) may fill the space between cap (33) and firing beam (460). Seal (480) includes an aperture (482) through which firing beam (460) may translate. Aperture (482) is shaped substantially similarly to the cross-section of firing beam (460). By way of example only, seal (480) is comprised of a soft relatively flexible material such as rubber, silicone, or the like. Accordingly, seal (480) is configured to seal off the distal end of shaft (30) while allowing firing beam (460) to freely translate relative to seal (480). In some instances, aperture (482) is slightly undersized relative to the cross-sectional profile of firing beam (460), such that seal (480) resiliently bears slightly against the outer surfaces of firing beam (460). Thus, as firing beam (460) is reciprocated through seal (480) may act as a squeegee and thereby wipe tissue, coagulated blood, bodily fluid, etc. from firing beam (460).

Seal (480) is further configured to be removable from aperture (31) of cap (33). For instance, in some examples electrode (450) and insulating member (451) may be removable as described above with respect to end effector (140). In such examples, seal (480) may be pulled from aperture (31) of shaft (30) along with electrode (450) and insulating member (451). To further increase the removability of seal (480), seal (480) includes an open portion (484). Open portion (484) in the present example may allow seal (480) to be removed transversely relative to firing beam (460) in addition to being pulled distally off of firing beam (460).

In an exemplary use, seal (480) is initially in place within aperture (31) of cap (33). End effector (440) may then be used to cut and/or seal tissue as described above. While end effector (440) is in use, seal (480) may prevent tissue and/or fluids from entering shaft (30). After end effector (440) has been used to cut and/or seal tissue, a user may remove electrode (450) and insulating member (451) from first jaw (442) of end effector (440). Removal of electrode (450) and insulating member (451) may also remove seal (480) from aperture (31) of cap (33). As seal (480) is pulled distally along firing beam (460), seal (480) may act as a squeegee and thereby wipe tissue, coagulated blood, bodily fluid, etc. from firing beam (460).

Figure 21:
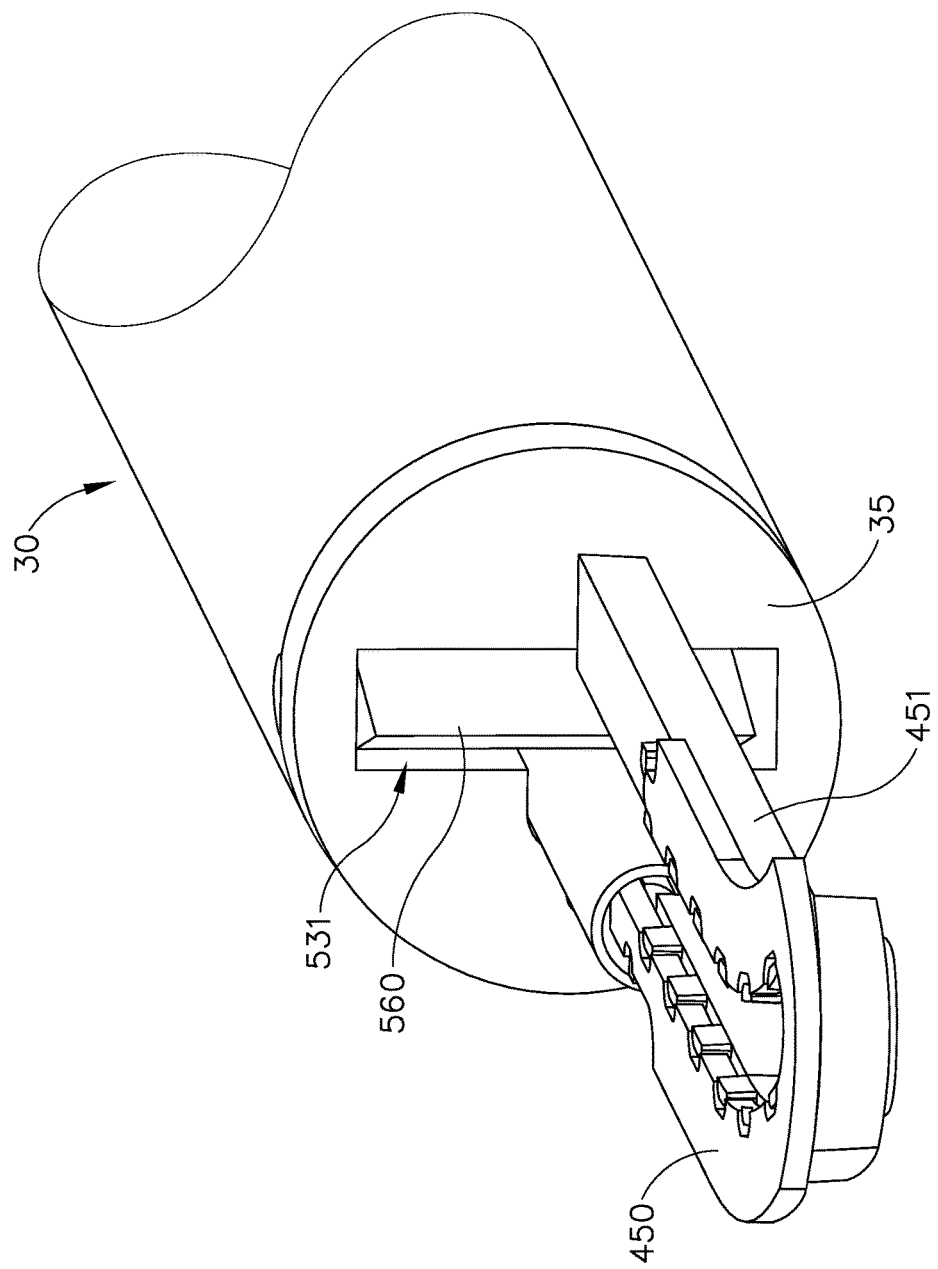
FIG. 21 depicts a perspective view of an exemplary alternative seal suitable for incorporation in the end effector of FIG. 18.

FIG. 21 shows an exemplary alternative seal (580) that may be used with end effector (440) described above. In particular, seal (580) is substantially the same as seal (480), except seal (580) of the present example is for configured for use with a firing beam (560) that lacks structures that are equivalent to flanges (62, 66). Firing beam (560) of this example thus has a simple rectangular cross-section along the region that passes through seal (480). As can be seen, the distal end of shaft (30) comprises a rectangularly shaped aperture (531) that corresponds to the rectangular cross-section of firing beam (560). Similar to aperture (31) described above, the aperture (531) of a cap (35) at the distal end of shaft (30) is larger than the cross-section of firing beam (560). Accordingly, seal (580) is sized to fill the space of aperture (531) between the distal end of shaft (30) and firing beam (560).

Figure 22:
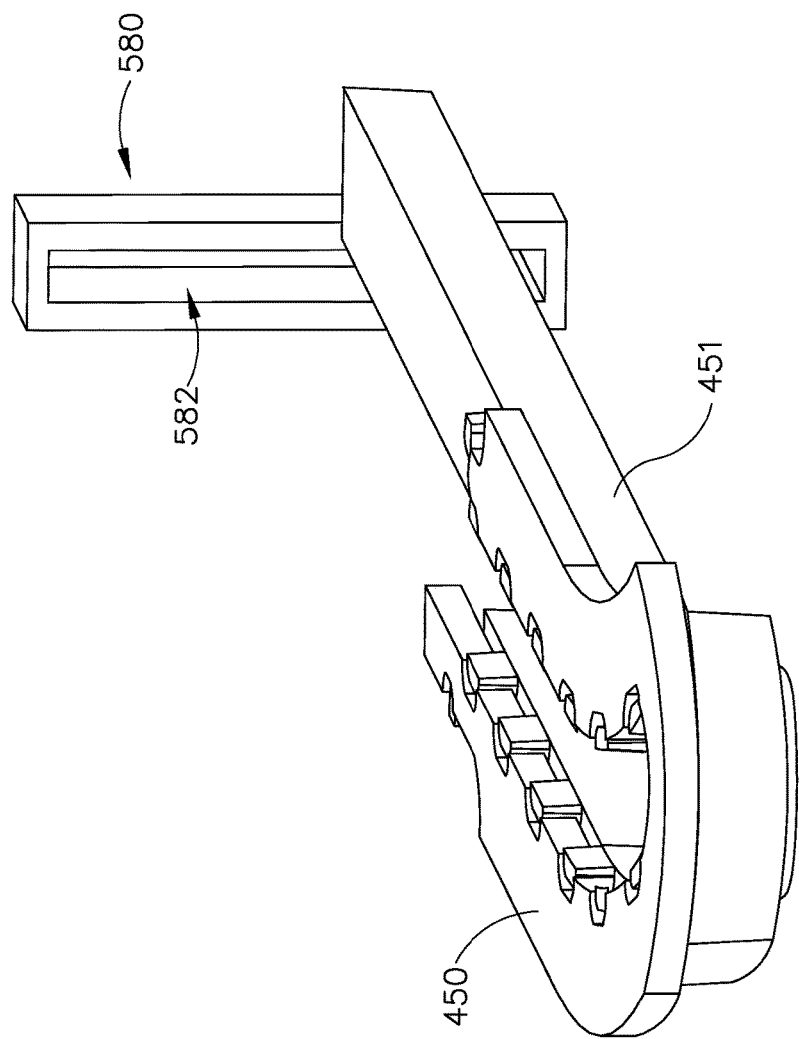
FIG. 22 depicts a perspective view of the seal of FIG. 21.

As can be seen in FIG. 22, seal (580) includes a relatively rectangularly shaped aperture (582), which functions similarly to aperture (482) described above. In some instances, aperture (582) is slightly undersized relative to the cross-sectional profile of firing beam (560), such that seal (580) resiliently bears slightly against the outer surfaces of firing beam (560). Thus, as firing beam (560) is reciprocated through seal (580) may act as a squeegee and thereby wipe tissue, coagulated blood, bodily fluid, etc. from firing beam (560). Although not shown, it should be understood that seal (580) may also include an open portion similar to open portion (484) described above. In some versions, seal (580) is unitarily secured to electrode (450) and insulating member (451). In such versions where electrode (450) and insulating member (451) are removable from shaft (30), when the operator removes the assembly of electrode (450), insulating member (451), and seal (580) from shaft (30), seal (580) may act as a squeegee and thereby wipe tissue, coagulated blood, bodily fluid, etc. from firing beam (560). Other suitable ways in which structures may be configured to serve as a seal and/or as a wiping element at the distal end of shaft (30) will be apparent to those of ordinary skill in the art in view of the teachings herein.

V. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, issued as U.S. Pat. No. 8,408,439 on Apr. 2, 2013; and U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2013. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, now abandoned, the disclosure of which is incorporated by reference herein; U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a shaft;
   (b) an end effector coupled to a distal end of the shaft, wherein the end effector comprises:
      (i) a first jaw,
      (ii) a second jaw, wherein the first jaw is selectively pivotable toward and away from the second jaw to capture tissue, and
      (iii) at least one electrode, wherein the at least one electrode is operable to apply RF energy to tissue captured between the first jaw and the second jaw;
   (c) a translating member configured to translate through the end effector; and
   (d) a removable portion, wherein the removable portion is selectively removable from a remaining portion of the apparatus to transition the apparatus into a cleaning state, wherein the remaining portion includes the shaft, the first and second jaws, and the translating member, wherein the removable portion includes:
      (i) the electrode,
      (ii) a wiper coupled with the electrode, wherein the wiper is configured to sealingly engage and thereby clean at least part of the translating member during removal of the removable portion from the remaining portion, and
      (iii) a support member, wherein the support member is coupled to the electrode and the wiper,
      wherein the electrode, the wiper, and the support member are configured to remain coupled with one another following removal of the removable portion from the remaining portion.

2. The apparatus of claim 1, further comprising a removal tool, wherein the removal tool includes at least one member configured to engage the end effector to transition the end effector into the cleaning state.

3. The apparatus of claim 2, wherein at least one of the jaws includes at least one channel, wherein the at least one channel corresponds to the at least one member of the removal tool.

4. The apparatus of claim 3, wherein the at least one member of the removal tool is insertable into the at least one channel to engage a portion of the end effector to remove at least a portion of the end effector thereby transitioning the end effector to the cleaning state.

5. The apparatus of claim 1, wherein the end effector further comprises at least one sensor and wherein the sensor is configured to obtain data indicating whether the end effector is in the cleaning state.

6. The apparatus of claim 1, wherein a proximal end of the end effector is insertable into the distal end of the shaft.

7. The apparatus of claim 1, wherein the wiper comprises a wiper seal positioned at a proximal end of the removable portion.

8. The apparatus of claim 7, wherein the wiper seal includes a resilient member disposed within the wiper seal.

9. The apparatus of claim 1, wherein the wiper is configured to seal the shaft relative to the end effector.

10. The apparatus of claim 1, wherein a distal end of the translating member is configured to extend between the first and second jaws.

11. The apparatus of claim 1, wherein the wiper defines a proximal end of the removable portion.

12. The apparatus of claim 1, further comprising a cap disposed within the distal end of the shaft, wherein the cap includes an aperture configured to removably receive the wiper therein.

13. An apparatus for operating on tissue, the apparatus comprising:
(a) a shaft;
(b) an end effector coupled to a distal end of the shaft, wherein the end effector comprises:
   (i) a first jaw,
   (ii) a second jaw, wherein the first jaw is selectively pivotable toward and away from the second jaw to capture tissue,
   (iii) an electrode, wherein the electrode is operable to apply RF energy to tissue captured between the first jaw and the second jaw, and
   (iv) a support member, wherein the electrode is coupled to and supported by the support member;
(c) a translating firing member operable to actuate the first and second jaws between an open state and a closed state, wherein the translating firing member is operable to extend distally between the first and second jaws;
(d) a cap disposed within a distal end of the shaft, wherein the cap includes an aperture; and
(e) a seal disposed within the aperture of the cap and coupled to the support member, wherein the seal is configured to sealingly engage the translating firing member,
wherein the electrode, the support member, and the seal collectively define a removable unit that is selectively removable from a remaining portion of the apparatus, wherein the remaining portion includes the shaft, the first jaw, and the second jaw.

14. The apparatus of claim 13, wherein the translating firing member comprises a blade configured to cut tissue.

15. The apparatus of claim 13, wherein the electrode includes a longitudinal slot configured to receive the translating firing member.

16. The apparatus of claim 13, wherein the support member extends distally relative to the seal.

17. An apparatus for operating on tissue, the apparatus comprising:
(a) an end effector, wherein the end effector comprises:
   (i) a first jaw,
   (ii) a second jaw, wherein the first jaw is selectively pivotable toward and away from the second jaw to capture tissue,
   (iii) an electrode, wherein the electrode is operable to apply RF energy to tissue captured between the first jaw and the second jaw, and
   (iv) a support member, wherein the electrode is coupled to and supported by the support member,
(b) a translating firing member operable to actuate the first and second jaws between an open state and a closed state; and
(c) a seal coupled with the electrode, wherein the seal has an aperture through which the translating firing member is configured to extend, wherein the seal is configured to sealingly engage the translating firing member throughout a full range of translation of the translating firing member relative to the end effector,
wherein the seal, the electrode, and the support member collectively define a removeable unit that is selectively removable from a remaining portion of the apparatus, wherein the remaining portion includes the first and second jaws and the translating firing member,
wherein the seal, the electrode, and the support member are configured to remain coupled with one another following removal of the removable unit from the remaining portion.

18. The apparatus of claim 17, wherein the seal is configured to fully surround a portion of the translating firing member extending through the aperture.

19. The apparatus of claim 17, further comprising a shaft and a cap, wherein the end effector is coupled to a distal end of the shaft, wherein the cap includes an aperture and is disposed within a distal end of the shaft, wherein the seal is disposed within the aperture.

20. The apparatus of claim 17, wherein the support member extends distally relative to the seal.

* * * * *